US008953857B2

(12) United States Patent
Kondo et al.

(10) Patent No.: US 8,953,857 B2
(45) Date of Patent: Feb. 10, 2015

(54) SIMILAR CASE SEARCHING APPARATUS AND SIMILAR CASE SEARCHING METHOD

(75) Inventors: Kenji Kondo, Kyoto (JP); Takashi Tsuzuki, Osaka (JP); Kazutoyo Takata, Osaka (JP)

(73) Assignee: Panasonic Corporation, Osaka (JP)

( * ) Notice: Subject to any disclaimer, the term of this patent is extended or adjusted under 35 U.S.C. 154(b) by 435 days.

(21) Appl. No.: 13/482,052

(22) Filed: May 29, 2012

(65) Prior Publication Data

US 2013/0006087 A1    Jan. 3, 2013

Related U.S. Application Data

(63) Continuation of application No. PCT/JP2011/006375, filed on Nov. 16, 2011.

(30) Foreign Application Priority Data

Jun. 30, 2011    (JP) ................................. 2011-146699

(51) Int. Cl.
*G06K 9/00*    (2006.01)
*G06F 19/00*    (2011.01)
*G06Q 50/22*    (2012.01)

(52) U.S. Cl.
CPC ............ *G06F 19/3443* (2013.01); *G06Q 50/22* (2013.01)
USPC ....................................................... 382/128

(58) Field of Classification Search
None
See application file for complete search history.

(56) References Cited

U.S. PATENT DOCUMENTS 6,564,202 B1    5/2003    Schuetze et al.
6,567,797 B1    5/2003    Schuetze et al.
(Continued)

FOREIGN PATENT DOCUMENTS

JP    2000-148793    5/2000
JP    2002-063280    2/2002
(Continued)

OTHER PUBLICATIONS

Müller, Henning, et al. "A review of content-based image retrieval systems in medical applications—clinical benefits and future directions." International journal of medical informatics 73.1 (2004): 1-23.*
(Continued)

*Primary Examiner* — Stephen R Koziol
*Assistant Examiner* — Raphael Schwartz
(74) *Attorney, Agent, or Firm* — Wenderoth, Lind & Ponack, L L P.

(57) ABSTRACT

A similar case searching apparatus comprising: a weight determining unit which determines the weight to each of feature quantities extracted from an interpretation target image, based on predetermined two-data correlation information defining the correlation between the feature quantity and one of at least one image interpretation item and a disease name both included in an image interpretation report of a medical image included in a case data item registered in a case database, such that the weight is larger as the correlation is higher; and a similar case searching unit which searches for a similar case data item including a similar image, by weighting, using the weight, each image feature quantity in a first set extracted from the interpretation target image and a corresponding one of the image feature quantities in a second set extracted from the medical image, and comparing the weighted first set and the weighted second set.

8 Claims, 24 Drawing Sheets

(56) References Cited

U.S. PATENT DOCUMENTS

| | | | |
|---|---|---|---|
| 6,598,054 | B2 | 7/2003 | Schuetze et al. |
| 6,728,752 | B1 | 4/2004 | Chen et al. |
| 6,922,699 | B2 | 7/2005 | Schuetze et al. |
| 6,925,199 | B2 | 8/2005 | Murao |
| 6,941,321 | B2 | 9/2005 | Schuetze et al. |
| 7,374,077 | B2 | 5/2008 | Shimura |
| 2002/0065460 | A1 | 5/2002 | Murao |
| 2003/0074368 | A1 | 4/2003 | Schuetze et al. |
| 2003/0074369 | A1 | 4/2003 | Schuetze et al. |
| 2003/0110181 | A1 | 6/2003 | Schuetze et al. |
| 2004/0003001 | A1 * | 1/2004 | Shimura ............ 707/104.1 |
| 2009/0097756 | A1 | 4/2009 | Kato |
| 2010/0256459 | A1 | 10/2010 | Miyasa et al. |
| 2011/0022622 | A1 | 1/2011 | Boroczky et al. |

FOREIGN PATENT DOCUMENTS

| | | |
|---|---|---|
| JP | 2002-230518 | 8/2002 |
| JP | 2004-005364 | 1/2004 |
| JP | 2004-157623 | 6/2004 |
| JP | 2006-318219 | 11/2006 |
| JP | 2007-275408 | 10/2007 |
| JP | 2009-082441 | 4/2009 |
| JP | 2009/093563 | 4/2009 |
| JP | 2010-082001 | 4/2010 |
| JP | 2010-250359 | 11/2010 |
| JP | 2010-250849 | 11/2010 |
| JP | 2011-508331 | 3/2011 |
| JP | 2011-118543 | 6/2011 |
| WO | 2009/083841 | 7/2009 |

OTHER PUBLICATIONS

Worring, Marcel, Arnold Smeulders, and Simone Santini. "Interaction in content-based image retrieval: An evaluation of the state-of-the-art." Advances in Visual Information Systems. Springer Berlin Heidelberg, 2000. 26-36.*

International Search Report issued Dec. 20, 2011 in International (PCT) Application No. PCT/JP2011/006375.

Jennifer G. Dy et al., "Unsupervised Feature Selection Applied to Content-Based Retrieval of Lung Images", IEEE Transactions on Pattern Analysis and Machine Intelligence, vol. 25, No. 3, Mar. 2003.

Mitsutaka Nemoto et al., "Improvement of Tumor Detection Performance in Mammograms by Feature Selection from a Large Number of Features and Proposal of Fast Feature Selection Method", IEICE Transactions on Information and Systems, D-II, vol. J88-D-II, No. 2, Feb. 2005, pp. 416-426, with partial English translation.

Misato Tamura et al., "Improvement of an extraction method of liver regions based on gray pattern of abnormal regions (2nd Report)", The Institute of Electronics, Information and communication Engineers, Technical Report of IEICE, Iyougazo, 104 (580), pp. 7-12, Jan. 2005.

Junya Nakagawa et al., "Development of an automated extraction method for liver tumors in three dimensional abdominal CT images", The Institute of Electronics, Information and communication Engineers, Technical Report of IEICE, Sep. 2002.

MeCab (http://mecab.sourceforge.net), Sep. 27, 2009.

ChaSen(http://chasen-legacy.sourceforge.jp), Oct. 13, 2007.

KNP(http://nlp.kuee.kyoto-u.ac.jp/nl-resource/knp.html), Oct. 6, 2011.

CaboCha(http://chasen.org/~taku/software/cabocha/), Jun. 2001.

Naoki Kato et al., "Data Mining and its Applications", Asakura Publishing Co., Ltd., Sep. 25, 2008.

* cited by examiner

FIG. 5

| Image interpretation item |
|---|
| Early stain |
| Washout |

| Disease name |
|---|
| Hepatocellular carcinoma |

FIG. 6

| Image interpretation item | Location | Time phase |
|---|---|---|
| Early stain | Liver segment S3 | — |
| Washout | — | Late phase |

| Disease name |
|---|
| Hepatocellular carcinoma |

FIG. 7

| Image interpretation item | Location | Time phase |
|---|---|---|
| Early stain | Liver segment S3 | Early phase |
| Washout | Liver segment S3 | Late phase |

| Disease name |
|---|
| Hepatocellular carcinoma |

FIG. 8

| Case number | | Lesion number | Feature quantity number | Value |
|---|---|---|---|---|
| 1 | Image feature quantity | (1, 1) | 1 | 0.851 |
| | | | 2 | 0.941 |
| | | | ⋮ | ⋮ |
| | | | $N_F$ | 0.066 |
| | | (1, 2) | 1 | 0.515 |
| | | | 2 | 0.050 |
| | | | ⋮ | ⋮ |
| | | | $N_F$ | 0.593 |
| | | ⋮ | 1 | 0.540 |
| | | | 2 | 0.487 |
| | | | ⋮ | ⋮ |
| | | | $N_F$ | 0.152 |
| | | (1, $M_1$) | 1 | 0.366 |
| | | | 2 | 0.895 |
| | | | ⋮ | ⋮ |
| | | | $N_F$ | 0.073 |
| | Image interpretation item | | (1, 1) | Early stain |
| | | | (1, 2) | Washout |
| | | | ⋮ | ⋮ |
| | | | (1, $N_1$) | High absorption |
| | Disease name | | | Hepatocellular carcinoma |
| ⋮ | | | | |
| C | Image feature quantity | (C, 1) | 1 | 0.703 |
| | | | 2 | 0.975 |
| | | | ⋮ | ⋮ |
| | | | $N_F$ | 0.564 |
| | | (C, 2) | 1 | 0.104 |
| | | | 2 | 0.013 |
| | | | ⋮ | ⋮ |
| | | | $N_F$ | 0.728 |
| | | ⋮ | 1 | 0.893 |
| | | | 2 | 0.489 |
| | | | ⋮ | ⋮ |
| | | | $N_F$ | 0.150 |
| | | (C, $M_C$) | 1 | 0.317 |
| | | | 2 | 0.077 |
| | | | ⋮ | ⋮ |
| | | | $N_F$ | 0.494 |
| | Image interpretation item | | (C, 1) | High absorption |
| | | | (C, 2) | Early stain |
| | | | ⋮ | ⋮ |
| | | | (C, $N_C$) | Afferent |
| | Disease name | | | Angioma |

FIG. 13

|  | Image feature quantity 1 | Image feature quantity 2 | Image feature quantity 3 | ... | Image feature quantity $N_{IF}$ |
|---|---|---|---|---|---|
| Image interpretation item 1 | 0.808 | 0.627 | 0.973 | ... | 0.304 |
| Image interpretation item 2 | 0.372 | 0.991 | 0.135 | ... | 0.782 |
| Image interpretation item 3 | 0.859 | 0.326 | 0.073 | ... | 0.152 |
| ... | ... | ... | ... | ... | ... |
| Image interpretation item $N_{II}$ | 0.166 | 0.237 | 0.576 | ... | 0.724 |

FIG. 14

| | Image feature quantity 1 | Image feature quantity 2 | Image feature quantity 3 | ... | Image feature quantity $N_{IF}$ |
|---|---|---|---|---|---|
| Disease name 1 | 0.671 | 0.697 | 0.298 | ... | 0.191 |
| Disease name 2 | 0.726 | 0.062 | 0.970 | ... | 0.785 |
| Disease name 3 | 0.365 | 0.129 | 0.085 | ... | 0.695 |
| ... | ... | ... | ... | ... | ... |
| Disease name $N_D$ | 0.277 | 0.238 | 0.897 | ... | 0.818 |

FIG. 15

| | Disease name 1 | Disease name 2 | Disease name 3 | ... | Disease name $N_D$ |
|---|---|---|---|---|---|
| Image interpretation item 1 | 23.06 | 47.58 | 9.58 | ... | 5.10 |
| Image interpretation item 2 | 1.41 | 6.21 | 32.96 | ... | 12.80 |
| Image interpretation item 3 | 0.95 | 9.80 | 3.94 | ... | 42.18 |
| ... | ... | ... | ... | ... | ... |
| Image interpretation item $N_{II}$ | 36.35 | 22.52 | 16.82 | ... | 23.94 |

FIG. 22
(a) Case of image interpretation report in which "Clear border" is written as image interpretation item
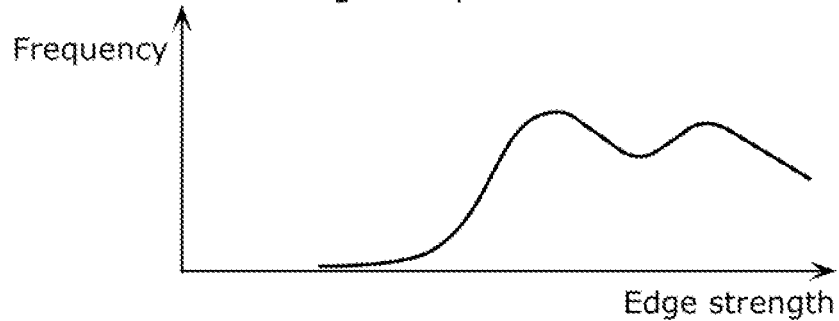
(b) Case of image interpretation report in which "Clear border" is not written as image interpretation item
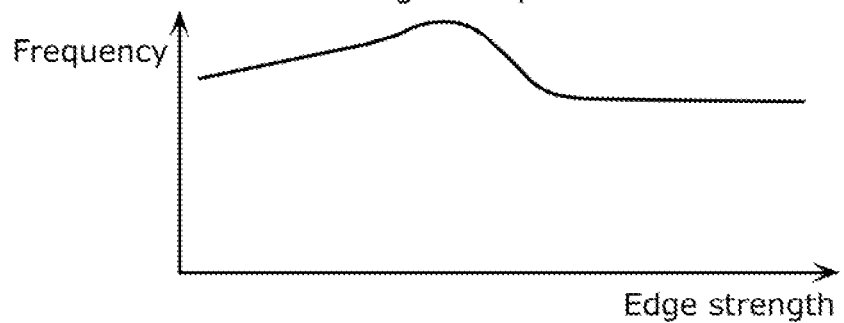

FIG. 23

| | Image feature quantity 1 | Image feature quantity 2 | Image feature quantity 3 | ... | Image feature quantity $N_{1F}$ |
|---|---|---|---|---|---|
| Image interpretation item 1 | $(p_1, p_2 \cdots p_{dim})$ | | | | |
| Image interpretation item 2 | | | | | |
| Image interpretation item 3 | | | | | |
| ... | | | | | |
| Image interpretation item $N_{II}$ | | | | | |

FIG. 24
(a) Case where disease name (diagnosis name) is "Hepatocellular carcinoma"
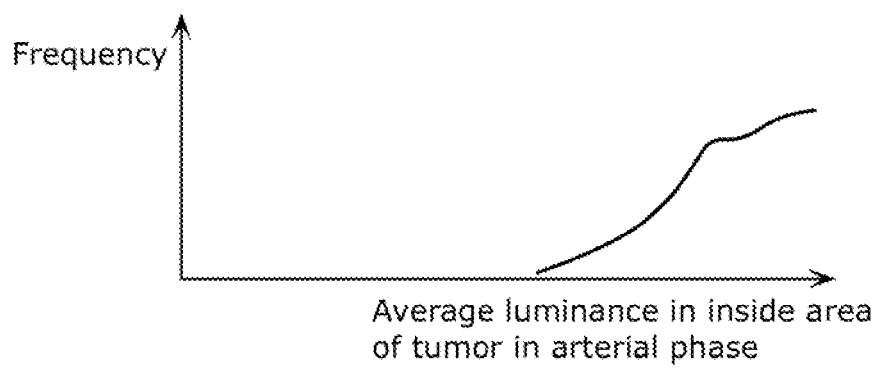
(b) Case where disease name (diagnosis name) is "cyst"
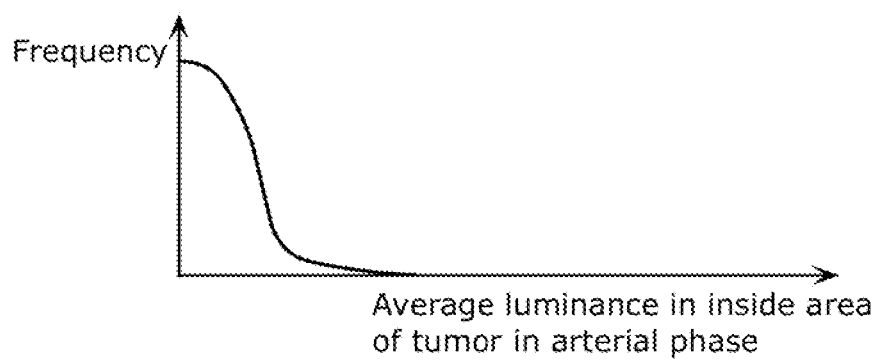

FIG. 25

|  | Image feature quantity 1 | Image feature quantity 2 | Image feature quantity 3 | ... | Image feature quantity $N_{IF}$ |
|---|---|---|---|---|---|
| Disease name 1 | $(p_1, p_2 \cdots p_{dim})$ |  |  |  |  |
| Disease name 2 |  |  |  |  |  |
| Disease name 3 |  |  |  |  |  |
| ... |  |  |  |  |  |
| Disease name $N_D$ |  |  |  |  |  |

FIG. 26

Low absorption area with clear border is observed in liver segment S3 and no contrast effect is observed, therefore liver cyst is suspicious.

Distribution of values of "Edge strengths" as image feature quantities in case of image interpretation report in which "Clear border" is written as image interpretation item

SIMILAR CASE SEARCHING APPARATUS AND SIMILAR CASE SEARCHING METHOD

CROSS REFERENCE TO RELATED APPLICATIONS

This is a continuation application of PCT Patent Application No. PCT/JP2011/006375 filed on Nov. 16, 2011, designating the United States of America, which is based on and claims priority of Japanese Patent Application No. 2011-146699 filed on Jun. 30, 2011. The entire disclosures of the above-identified applications, including the specifications, drawings and claims are incorporated herein by reference in their entirety.

TECHNICAL FIELD

Apparatuses and methods consistent with one or more exemplary embodiments of the present disclosure relate generally to similar case searching apparatuses and similar case searching methods for searching out a similar case that is useful as a reference for an interpretation of an image for medical use (a medical image).

BACKGROUND ART

Recent development and wide spread use of medical image capturing apparatuses for Computed Tomography (CT) and Magnetic Resonance Imaging (MRI) have made it possible to obtain a large volume of high-definition digital images for medical use. Furthermore, medical images already interpreted by doctors are increasingly accumulated one by one together with the image interpretation reports thereof in Picture Archiving and Communication Systems (PACS). In order to interpret a target image with reference to medical images similar to the target image, a start is made for development of techniques for searching out the similar images (medical images) from already-accumulated past cases.

How to select appropriate image feature quantities used to determine the similarity between medical images is important in similar image searches. A technique disclosed in the form of a conventional image searching apparatus is described below.

Image feature quantities for determining the similarity between the medical images should vary depending on the kinds of diseases, the progress (stages) of the diseases or the seriousness of the diseases, and the like. However, such conventional medical image searches use the same image feature quantities irrespective of the statuses of the diseases. Non-patent Literature 1 proposes a searching approach composed of two steps that are "customized-queries" approach (CQA) as a means for solving this problem. The first step of this approach is to classify query images using image feature quantities for classifying the classes of the kinds of diseases, the progress of the diseases or the seriousness of the diseases, and the like in the optimum manner. The second step of this approach is to search similar images using the image feature quantities optimized for further classification of the cases included in each of the classes obtained as a result of the previous classification. At this time, the image feature quantities optimum for the classes are calculated in advance through unsupervised learning. Furthermore, the technique disclosed in the Non-patent Literature 1 applies CQA for a lung CT images and to thereby achieve a search recall factor increased from those obtainable in such conventional similar image searches using only a single kind of image feature quantities.

CITATION LIST

Non Patent Literature

[NPL 1]
Jennifer G. Dy et al. "Unsupervised Feature Selection Applied to Content-based Retrieval of Lung Images", IEEE Transactions on Pattern Analysis and Machine Intelligence, vol. 25, no. 3, March 2003

SUMMARY OF INVENTION

Technical Problem

However, the apparatus in Non-patent Literature 1 merely determines image feature quantities (that are the reference for similarity determinations) based on the identified kinds of the diseases and the identified progress or seriousness of the diseases, and the like, and searches out similar images using the determined image feature quantities. Thus, the apparatus cannot perform a similar image search in which doctor focus points on the target image are reflected. In other words, the apparatus cannot sufficiently support the doctor when the doctor wish to get bases for his or her diagnosis or when the doctor has difficulty in making his or her diagnosis.

Solution to Problem

The similar case searching apparatus according to one or more exemplary embodiments of the present disclosure reflects user (such as doctor) focus points in a similar image search. One or more exemplary embodiments of the present disclosure may overcome the above disadvantage and other disadvantages not described herein. However, it is understood that one or more exemplary embodiments of the present disclosure are not required to overcome or may not overcome the disadvantage described above and other disadvantages not described herein.

The similar case searching apparatus according to one or more exemplary embodiments of the present disclosure searches a case database for a similar case data item similar to a target case data item of a target case to be diagnosed, the case database storing a plurality of case data items, each of the case data items and the target case data item including one or more medical images and an image interpretation report that is a document data item indicating interpretations of the medical images, and the similar case searching apparatus comprises: an image feature quantity extracting unit configured to extract a plurality of image feature quantities from one of the medical images which is an interpretation target image; a report analyzing unit configured to extract one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image; a weight determining unit configured to determine a weight to each of the image feature quantities extracted by the image feature quantity extracting unit, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and a similar case searching unit configured to search the case database for the similar case data item including a similar image similar to the interpretation target image, by weighting each of the image feature quantities in a first set extracted from the interpretation target image by the image feature quantity extracting unit and a corresponding one of the image feature quantities in a second set extracted from the medical images included in the case data items registered in the case database, using the weight to the image feature quantity determined by the weight determining unit, and comparing the weighted image feature quantities in the first set and the weighted image feature quantities in the second set.

It is to be noted that each of general or specific embodiments of the present disclosure may be implemented or realized as a system, a method, an integrated circuit, a computer program, or a recording medium, and that (each of) the specific embodiments may be implemented or realized as an arbitrary combination of (parts of) a system, a method, an integrated circuit, a computer program, or a recording medium.

Advantageous Effects of Invention

According to various exemplary embodiments of the present disclosure, it is possible to provide similar case searching apparatuses capable of reflecting user focus points on similar image searches.

BRIEF DESCRIPTION OF DRAWINGS

These and other advantages and features of exemplary embodiments of the present disclosure will become apparent from the following description thereof taken in conjunction with the accompanying Drawings that illustrate general and specific exemplary embodiments of the present disclosure. In the Drawings:

FIG. 5 is a table of image interpretation items and a disease name extracted from the image interpretation report according to Embodiment 1;

FIG. 6 is a table of image interpretation items and a disease name extracted from the image interpretation report according to Embodiment 1, and positions and time phases extracted together with the image interpretation items;

FIG. 7 is a table of image interpretation items and a disease name extracted from the image interpretation report according to Embodiment 1, and positions and time phases extracted together with the image interpretation items by performing context interpretation;

FIG. 8 is a table of a set of data items obtained for the extraction of information from image interpretation knowledge according to Embodiment 1;

FIG. 13 is a table (a storage format) of correlations between image feature quantities and image interpretation items extracted as image interpretation knowledge according to Embodiment 1;

FIG. 14 is a table (a storage format) of correlations between image feature quantities and disease names extracted as image interpretation knowledge according to Embodiment 1;

FIG. 15 is a table (a storage format) of correlations between image interpretation items and disease names extracted as image interpretation knowledge according to Embodiment 1;

FIG. 22 is composed of (a) and (b) that are graphs showing image feature quantity distributions different from each other depending on the presence/absence of an image interpretation item according to Embodiment 2 of the present disclosure;

FIG. 23 is a table of parameters of the image feature quantity distributions represented in the graphs of FIG. 22 according to Embodiment 2;

FIG. 24 is composed of (a) and (b) that are graphs showing image feature quantity distributions different from each other depending on the presence/absence of a disease name according to Embodiment 2;

FIG. 25 is a table of parameters of the image feature quantity distributions represented in the graphs of FIG. 24 according to Embodiment 2;

FIG. 26 is a diagram showing an example of an image interpretation report regarding an abdominal CT scan according to Embodiment 2;

DESCRIPTION OF EMBODIMENTS

Figure 1:
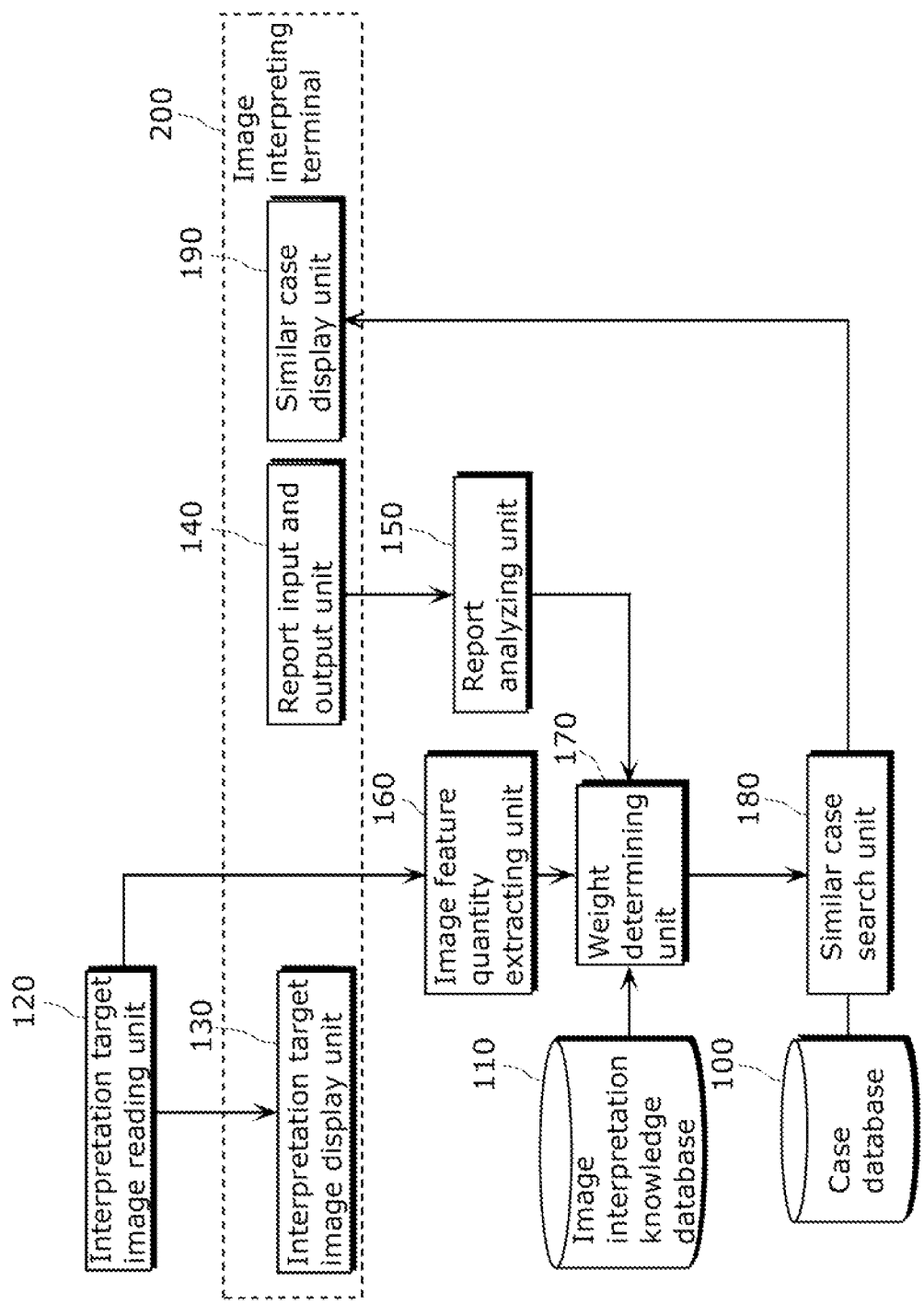
FIG. 1 is a block diagram of a structure of a similar case searching apparatus according to Embodiment 1 of the present disclosure.

The similar case searching apparatus according to one or more exemplary embodiments of the present disclosure searches a case database for a similar case data item similar to a target case data item of a target case to be diagnosed, the case database storing a plurality of case data items, each of the case data items and the target case data item including one or more medical images and an image interpretation report that is a document data item indicating interpretations of the medical images, and the similar case searching apparatus comprises: an image feature quantity extracting unit configured to extract a plurality of image feature quantities from one of the medical images which is an interpretation target image; a report analyzing unit configured to extract one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image; a weight determining unit configured to determine a weight to each of the image feature quantities extracted by the image feature quantity extracting unit, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and a similar case searching unit configured to search the case database for the similar case data item including a similar image similar to the interpretation target image, by weighting each of the image feature quantities in a first set extracted from the interpretation target image by the image feature quantity extracting unit and a corresponding one of the image feature quantities in a second set extracted from the medical images included in the case data items registered in the case database, using the weight to the image feature quantity determined by the weight determining unit, and comparing the weighted image feature quantities in the first set and the weighted image feature quantities in the second set.

With this structure, the similar case is searched out by weighting each of the image feature quantities extracted as a first set from the interpretation target image and a corresponding one of the image feature quantities extracted as a second set from the similar image such that the weight is larger as the correlation between the extracted image feature quantity and the selected one of the at least one image interpretation item and the disease name is higher, and comparing the weighted sets of the feature quantities. In this way, it is possible to perform the search for the similar case by reflecting the user focus point input in the target image interpretation report.

For example, the two-data correlation information may further indicate a correlation between the at least one image interpretation item and the disease name extracted from the image interpretation report, and when the report analyzing unit extracts, for a current one of the image feature quantities extracted by the image feature quantity extracting unit, both of the at least one image interpretation item and the disease name from the target image interpretation report, the weight determining unit may be configured to determine, as the weight to the current image feature quantity, a product of a value indicating a correlation between the current image feature quantity and the at least one image interpretation item extracted by the report analyzing unit and a value indicating a correlation between the at least one image interpretation item and the disease name extracted by the report analyzing unit, based on the two-data correlation information for the current image feature quantity.

With this structure, it is possible to perform the similar case search in which the correlations between the respective image feature quantities and the image interpretation item and the correlation between the image interpretation item and the disease name are evaluated at the same time when both of the image interpretation item and the disease name are input in the target image interpretation report.

In addition, when the report analyzing unit extracts, for a current one of the image feature quantities extracted by the image feature quantity extracting unit, the at least one image interpretation item from the target image interpretation report, the weight determining unit may be configured to determine, as the weight to the current image feature quantity, a value indicating a correlation between the current image feature quantity and the at least one image interpretation item extracted by the report analyzing unit, based on the two-data correlation information for the current image feature quantity.

With this structure, it is possible to perform the appropriate similar case search in the state where the user cannot make a final diagnosis including the disease name based on the image interpretation item that should be focused on by the user and wishes to make the final diagnosis based on a hit that is obtainable as a result of the similar case search.

In addition, when the report analyzing unit extracts, for a current one of the image feature quantities extracted by the image feature quantity extracting unit, the disease name from the target image interpretation report, the weight determining unit may be configured to determine, as the weight to the current image feature quantity, a value indicating a correlation between the at least one image interpretation item and the disease name extracted by the report analyzing unit, based on the two-data correlation information for the current image feature quantity.

With this structure, it is possible to perform the appropriate similar case search in the state where the user cannot make determinations on which one or more image interpretation items are the bases for the estimation of the disease name made based on user's intuition or the like. The user can get a hit for the bases (image interpretation items) for the diagnosis as a result of the similar case search.

In addition, the weight determining unit may be further configured to determine that each of the at least one image interpretation item extracted by the report analyzing unit has a higher validity as a current one of the image feature quantities corresponding to the at least one image interpretation item and extracted by the image feature quantity extracting unit has a higher likelihood, based on a probability distribution data prepared for a corresponding image feature quantity included in a medical image based on which an image interpretation report including at least one corresponding image interpretation item is made.

With this structure, it is possible to determine the validity of the image interpretation item written in the target image interpretation report and used for the similar case search.

The similar case searching apparatus may further comprise a display unit configured to display the target image interpretation report, wherein the display unit may be configured to display the at least one image interpretation item included in the target image interpretation report in a visually distinguishable manner, based on a degree of validity of the at least one image interpretation item determined by the weight determining unit.

With this structure, among the image interpretation items written in the target image interpretation report and used for the similar case search, it is possible to present, to the user, the bases for the similar case search and one or more image interpretation report portions (one or more image interpretation items) each having a low validity by displaying the one or more portions each having the low validity and one or more portions each having a high validity in a distinguishable manner.

In addition, the weight determining unit may be further configured to determine that the disease name extracted by the report analyzing unit has a higher validity as a current one of the image feature quantities corresponding to the disease name and extracted by the image feature quantity extracting unit has a higher likelihood, based on a probability distribution data prepared for a corresponding image feature quantity included in a medical image based on which an image interpretation report including the disease name is made.

With this structure, it is possible to determine the validity of the disease name written in the target image interpretation report and used for the similar case search.

The similar case searching apparatus may further comprise a display unit configured to display the target image interpretation report, wherein the display unit is configured to display the disease name included in the target image interpretation report in a visually distinguishable manner, based on a degree of validity of the disease name determined by the weight determining unit.

With this structure, among the disease names written in the target image interpretation reports and used for the similar case searches, it is possible to present, to the user, the bases for the similar case searches and one or more image interpretation report portions each having a low validity by displaying the one or more image interpretation report portions each having the low validity and one or more portions each having a high validity in a distinguishable manner.

It is to be noted that each of the general or specific embodiments of the present disclosure may be implemented or realized as a system, a method, an integrated circuit, a computer program, or a recording medium, and that (each of) the specific embodiments may be implemented or realized as an arbitrary combination of (parts of) a system, a method, an integrated circuit, a computer program, or a recording medium.

Hereinafter, exemplary embodiments of the present disclosure are described with reference to the Drawings. Each of the embodiments described below shows an example of the present disclosure. The numerical values, structural elements, the arrangement and connection of the structural elements, steps, the processing order of the steps etc. shown in the following embodiments are mere examples, and therefore do not limit the scope of the inventive concept, the scope of which is defined in the appended Claims and their equivalents. Among the structural elements in the following embodiments, the structural elements not recited in any one of the independent Claims defining the most generic concept of the present invention are described as optional structural elements in the embodiments.

Embodiment 1

FIG. 1 is a block diagram of a structure of a similar case searching apparatus according to Embodiment 1 of the present disclosure.

A similar case searching apparatus comprising: a case database 100, an image interpretation knowledge database 110, an interpretation target image reading unit 120, an interpretation target image display unit 130, a report input and output unit 140, a report analyzing unit 150, an image feature quantity extracting unit 160, a weight determining unit 170, a similar case search unit 180, and a similar case display unit 190.

The case database 100 is a database storing a plurality of case data items (hereinafter simply referred to as "cases"). Each of the case data item is composed of one or more medical images (in this Description, "image data" is simply referred to as an "image") and an image interpretation report that is the result of interpretation of the medical images). Such a medical image is an image used for Computer Tomography (CT), Magnetic Resonance Imaging (MRI), or the like. The image interpretation knowledge database 110 is a database storing image interpretation knowledge obtained by analyzing a plurality of cases. This image interpretation knowledge database 110 is described in detail later. The case database 100 and the image interpretation knowledge database 110 are stored in a recording device such as a Hard Disk Drive (HDD).

The interpretation target image reading unit 120 reads the images captured by a medical image capturing apparatus for CT, MRI, or the like from the medical image capturing apparatus or a storage device connected from outside.

The interpretation target image display unit 130 is composed of a medical-use high-definition monitor or the like, and displays the interpretation target image read by the interpretation target image reading unit 120.

The report input and output unit 140 is composed of an input means such as a keyboard and a mouse and a display means for allowing a user (such as a doctor) to confirm his or her inputs by displaying an image interpretation report portions input using the input means. The user inputs the image interpretation report portions through the report input and output unit 140 with reference to the interpretation target image displayed by the interpretation target image display unit 130.

The interpretation target image display unit 130, the report input and output unit 140, and the similar case display unit 190 that is described later constitute an image interpreting terminal 200.

The report analyzing unit 150 analyzes the image interpretation report input by the report input and output unit 140, and extracts text feature quantities (image interpretation items and a disease name).

The image feature quantity extracting unit 160 extracts a plurality of kinds of image feature quantities from the interpretation target image read by the interpretation target image reading unit 120.

The weight determining unit 170 determines weights respectively added to the image feature quantities to be used to search for images, based on the text feature quantities extracted by the report analyzing unit 150, the image feature quantities extracted by the image feature quantity extracting unit 160, and the image interpretation knowledge stored in the image interpretation knowledge database 110.

The similar case search unit 180 searches the case database 100 for a case including medical images similar to the interpretation target image, utilizing the image feature quantities extracted by the image feature quantity extracting unit 160 and the weights determined by the weight determining unit 170.

The similar case display unit 190 displays the similar case searched out by the similar case search unit 180. The similar case display unit 190 may be separately configured with a device of the same model as that of the high-definition monitor constituting the interpretation target image display unit 130. Furthermore, the interpretation target image and the similar case may be displayed on the high-definition monitor constituting the interpretation target image display unit 130 at the same time. Here, the similar case display unit 190 and the interpretation target image display unit 130 may be different in their device models.

Hereinafter, operations performed by the respective units according to this embodiment of the present disclosure are described in detail.

(Preparation of Image Interpretation Knowledge Database)

Prior to a similar case search, image interpretation knowledge is obtained in advance, and is stored in the image interpretation knowledge database 110. The image interpretation knowledge is generated to include a plurality of "cases" each of which is composed of medical images and the image interpretation report that is obtained as a result of the interpretation of the medical images. The similar case to be searched out and used here may be a case stored in the case database storing cases and used to search for the similar case, or a case stored in another database. The required number of cases should be a number sufficient to obtain a certain law and knowledge using various kinds of data mining algorithms. The number of data items is normally any number in a range from several hundreds to several tens of thousands. The image interpretation knowledge used in this embodiment is a correlation between two of three data types that are (i) the image feature quantity, (ii) the image interpretation item, and (iii) the disease name.

The "image feature quantities" relate to, for example, the shapes of organs or lesion portions in medical images, or the luminance distributions of the medical images. For example, Non-patent Literature 2 describes the use of four hundred and ninety kinds of feature quantities (Non-patent Literature 2: "Improvement of Tumor Detection Performance in Mammograms by Feature Selection from a Large Number of Features and Proposal of Fast Feature Selection Method", by Nemoto, Shimizu, Hagihara, Kobatake, and Nawano, The Journal of the Institute of Electronics, Information and Communication Engineers (J. IEICE) D-II, Vol. J88-D-II, No, 2, pp. 416-426, February 2005). As image feature quantities used in this embodiment, several ten to several hundred kinds of image feature quantities are predefined for each of medical image capturing apparatuses (modality apparatuses) used to capture the medical images or each of target organs used for image interpretation.

An "image interpretation item" is defined in this Description as a "character string made by a user (such as a doctor) as verbally indicating a feature of an interpretation target image". Terms that are used as image interpretation items are limited within certain ranges for the respective medical image capturing apparatuses, target organs, or the like. Examples of the image interpretation items include: Lobular, Spinal, Irregular, Clear border, Unclear contour, Low density, High density, Low absorption, High absorption, Ground-glass opacity, Calcification, Mosaic pattern, Early stain, Low echo, High echo, and Fuzz.

A "disease name" is the name of a disease diagnosed by the user (such as the doctor) based on medical images and other medical tests. The name of the disease diagnosed in the image interpretation may be different from the disease in the definitive diagnosis made after the other medical tests. Thus, the definitive diagnosis is used to generate the image interpretation knowledge database.

Hereinafter, a procedure for generating the image interpretation knowledge is described with reference to the flowchart of FIG. 2. It is assumed that the medical image capturing apparatus that is used in this embodiment is a multi-slice CT apparatus, and that a target organ and a target disease are a liver and a liver tumor, respectively.

In Step S10, a case is obtained from a database storing cases for obtaining image interpretation knowledge. Here, the total number of cases for obtaining the image interpretation knowledge is assumed to be C. A case is composed of medical images and an image interpretation report obtained as a result of the interpretation of the medical images. When the medical images are obtained by the multi-slice CT apparatus, the case includes several slice images. Normally, when a doctor interprets such multi-slice CT images, one to several important slice images among the slice images are attached to the corresponding image interpretation report as key images. Hereinafter, a set of several slice images or several key images are simply referred to as "medical images" or "images".

In Step S11, image feature quantities are extracted from the medical images. The process in Step S11 is described in detail with reference to the flowchart of FIG. 3.

In Step S111, an area of a target organ is extracted. In this embodiment, an area of a liver is extracted. As an example of a liver area extracting approach, the following approach can be used: Non-patent Literature 3: "Improvement of an extraction method of liver regions based on gray pattern of abnormal regions (2nd Report)", Tamura, Shimizu, and Kobatake, The Technical Report of IEICE, Medical Image, 104 (580), pp. 7-12, January 2005.

In Step S112, a lesion portion is extracted from the organ area extracted in Step S111. In this embodiment, a tumor portion of the liver area is extracted. As an example of a liver tumor portion extracting approach, the following approach can be used: Non-patent Literature 4: "Development of an automated extraction method for liver tumors in three dimensional abdominal CT images (2nd Report)", Nakagawa, Shimizu, Hitosugi, and Kobatake, The Technical Report of IEICE, Medical Image, 102 (575), pp. 89-94, January 2003. Here, assuming that the number of tumors extracted from the images in an i-th case is $M_i$, each of the tumors can be identified as a pair (i, j) where i denotes the case number and j denotes the tumor number. Here, $1 \leq i \leq C$ and $1 \leq j \leq M_i$ are satisfied. The name "tumor number" is used because the target lesion in this embodiment is the liver tumor. However, the "tumor number" may be referred to as a "lesion number" that is the common term in the present disclosure.

In Step S113, one of the lesion portions extracted in Step S112 is selected.

In Step S114, an image feature quantity is extracted from the lesion portion selected in Step S113. In this embodiment, some feature quantities applicable for the liver tumor are selected, for use, from among the four hundred and ninety kinds of image feature quantities described in Non-patent Literature 2: "Improvement of Tumor Detection Performance in Mammograms by Feature Selection from a Large Number of Features and Proposal of Fast Feature Selection Method", by Nemoto, Shimizu, Hagihara, Kobatake, and Nawano, The Journal of the Institute of Electronics, Information and Communication Engineers (J. IEICE) D-II, Vol. J88-D-II, No, 2, pp. 416-426, February 2005). The number of these feature quantities is assumed to be $N_F$. The feature quantities extracted in this step can be identified as a set (i, j, k) where i denotes the case number, j denotes the tumor number extracted from this case (medical image), and k denotes the feature number. Here, $1 \leq i \leq C$, $1 \leq j \leq M_i$, and $1 \leq k \leq N_F$ are satisfied.

In Step S115, a check is made to detect whether or not any unselected lesion portion remains among the lesion portions extracted in Step S112. When an unselected lesion portion remains, a return is made to Step S113 and the unselected lesion portion is selected and then Step S114 is executed again. When no unselected lesion portion remains, in other words, when a feature quantity selection in Step S114 is already made for all the lesion portions extracted in Step S112, the processes in the flowchart of FIG. 3 are completed, and a return is made to the flowchart of FIG. 2.

Figure 2:
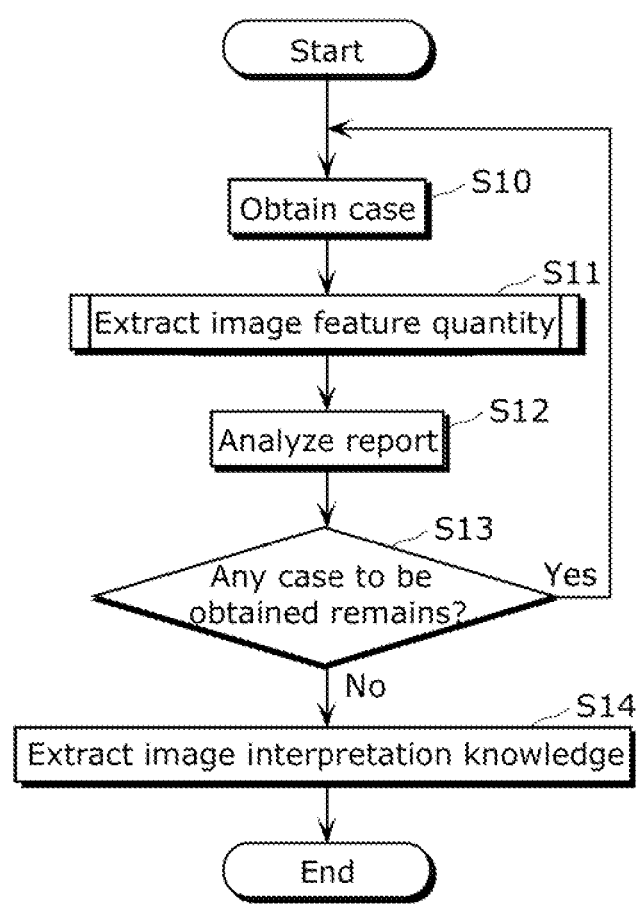
FIG. 2 is a flowchart of a procedure for generating image interpretation knowledge according to Embodiment 1.

In Step S12 of FIG. 2, a process for analyzing an image interpretation report is performed. More specifically, the image interpretation items and the disease name are extracted from the image interpretation report. In this embodiment, a morpheme analysis and a syntax analysis are made using an image interpretation item word dictionary in which image interpretation items are stored and a disease name word dictionary in which disease names are stored. Through these processes, words, matching the words stored in the respective word dictionaries are extracted. Examples of morpheme analysis techniques include Non-patent Literatures 5 and 6: MeCab (http://mecab.sourceforge.net) and chasen-legacy-.sourceforge.jp), and examples of syntax analysis techniques include Non-patent Literatures 7 and 8: KNP (http://nlp-.Kuee.kyoto-u.Ac.jp/nl-resource/knp.html), CaboCha (http://chasen.org/~taku/software/cabocha/). Image interpretation reports are often written by doctors using expressions unique to image interpretation reports. Thus, it is desirable to develop morpheme analysis techniques, syntax analysis techniques, and various words dictionaries exclusive for image interpretation reports.

Figures 3, 4:
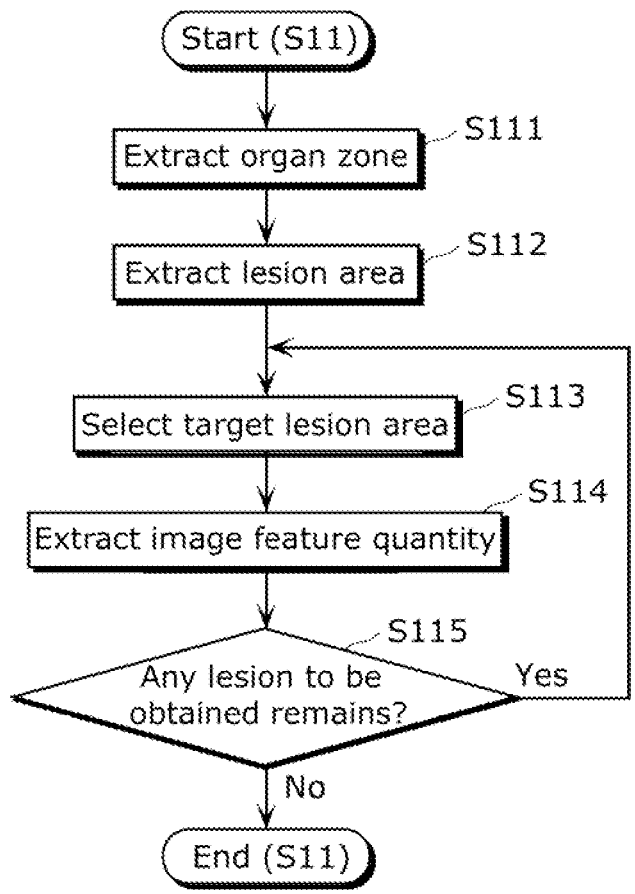
FIG. 3 is a flowchart of a procedure for extracting image feature quantities according to Embodiment 1.
FIG. 4 is a diagram showing an example of a portion of an image interpretation report regarding an abdominal CT scan according to Embodiment 1.

FIG. 4 is an example of an image interpretation report of an abdominal CT scan. FIG. 5 shows image interpretation items and a disease name extracted from the image interpretation report in FIG. 4. Several image interpretation items are normally extracted while one disease name is extracted. Assuming that the number of image interpretation items extracted from the image interpretation report in the i-th case is $N_i$, each of the image interpretation items can be identified as a pair (i, j) where i denotes the case number, and j denotes the image interpretation item number. Here, $1 \leq i \leq C$ and $1 \leq j \leq N_i$ are satisfied.

In addition, although only the words related to the image interpretation items and disease name are extracted in FIG. 5, it is also possible to extract character strings indicating the positions of lesions in the image interpretation report and character strings indicating time phases at the same time. Here, supplemental information regarding the time phases is provided. It is considered that a contrast radiography for time-series image capturing using a rapid intravenous injection is useful for identifying a lesion in a liver. In a contrast radiography of a liver, images of the liver are generally captured in the following time phases: an arterial phase in which a contrast medium is infused into a liver artery and a stain of a hypervascular tumor is observed; a portal venous phase in which the contrast medium distributed in an intestinal tract and a spleen is infused from a portal vein to the liver, and a hepatocyte has a highest contrast; an equilibrium phase in which the contrast medium inside and outside the blood vessels of the liver reaches its equilibrium; and a late phase in which the contrast medium stays in a stroma of the liver. Image interpretation reports often include descriptions of information about the positions of lesions in organs, and information about time phases focused in contrast radiography. For this reason, the information about the positions and the information about the time phases extracted together with the image interpretation items are effective in the extraction of necessary information from the image interpretation knowledge described later. FIG. 6 shows an example where the information about positions and the information about time phases are extracted together with image interpretation items. For example, in the case of an analysis of an image interpretation report in FIG. 4, from a sentence clause that "Early stain is observed in liver segment S3", the "Liver segment S3" is extracted as a position attribute of the "Early stain". Likewise, from a sentence clause that "Washout is observed in late phase", the "Late phase" is extracted as a time phase attribute of "Washout".

When the image interpretation report in FIG. 4 is simply interpreted, the column for the time phase related to the "Early stain" and the column for the position related to the "Washout" are blanks in the table of FIG. 6. On the other hand, when it is possible to utilize prepared knowledge that the image interpretation item "Early stain" is a term related to the early phase and to perform a context analysis that the tumor indicating the state of the "Early stain" refers to the tumor that is washed out in the "Late phase", the information about the position and the information about the time phase extracted in this case are as shown in FIG. 7.

In Step S13, a check is made to detect whether or not any case to be obtained remains in the database storing cases for obtaining information from image interpretation knowledge. When a case to be obtained remains, a return is made to Step S10, the case is obtained, and Steps S11 and S12 are executed. When no case to be obtained remains, in other words, an image feature extraction in Step S11 and a report analysis in Step S12 are already completed for each of all the cases, a transition to Step S14 is made.

The results obtained through Step S11 and Step S12 are independent of each other, and thus the execution order may be reversed.

At the time point at which Step S14 is reached, for example, a set of data items shown in FIG. 8 is obtained. In other words, the image feature quantities, the image interpretation items, and the disease name are obtained for each of the cases. The case assigned with the case number 1 includes an M1 number of lesions in one or more medical images, and the number of image feature quantities to be extracted from each of the lesions is denoted as NF. Furthermore, the number of image interpretation items in the image interpretation report of the case number 1 is denoted as N1. For example, in the first lesion shown as a lesion number 1 in a set of numbers (1, 1), the value of the first image feature quantity is 0.851. In addition, the value of the first image interpretation item shown as an image interpretation item number 1 in the set of numbers (1, 1) shows "Early stain". In the example of FIG. 8, each of the image feature quantities is any numerical value within a range from 0 to 1 inclusive, and each of the image interpretation items and the disease name is a character string. It is also good to use a negative value or a value larger than 1 as an image feature quantity. Furthermore, it is also good to store each of the image interpretation items and the disease name as a data item in the form of a predefined word ID.

In Step S14, image interpretation knowledge is extracted from the image feature quantities obtained in Step S11 and the image interpretation items and the disease name obtained in Step S12. In this embodiment, the image interpretation knowledge is the correlation between two of the three data types of the image feature quantity, the image interpretation item, and the disease name.

Hereinafter, descriptions are given of two types of correlations that are obtained from any two of the three data types of the image feature quantity, the image interpretation item, and the disease name.

(1) Correlation between Image Feature Quantity and Image Interpretation Item

A description is given of how to calculate the correlation between an image feature quantity and an image interpretation item in a pair. A correlation ratio is used here from among several kinds of representation forms of correlations. A correlation used here is an index indicating the correlation between a qualitative data item and a quantitative data item, and is presented in Expression 1.

[Math. 1]

$$\eta^2 = \frac{\sum_i N_i(\overline{x}_i - \overline{x})^2}{\sum_i \sum_j (x_{ij} - \overline{x})^2} = \frac{S_B}{S_T} \quad \text{(Expression 1)}$$

Here, $x_{ij}$ is an i-th observed value that belongs to a category of the qualitative data.

$\overline{x}_i$ denotes the average value of observed values that belong to the category i of the qualitative data;

$\overline{x}$ denotes the overall average value;

$N_i$ denotes the number of observations that belong to the category i;

$S_B$ denotes an inter-category dispersion; and $S_T$ denotes a total dispersion.

Image interpretation reports are classified into two categories based on the presence/absence of a certain image interpretation item, and these categories are assumed to be qualitative data items. The raw values of image feature quantities of a kind extracted from the medical images are assumed to be qualitative data items. For example, for each of the cases included in the case database for extracting image interpretation knowledge, the image interpretation reports are classified into the categories one of which includes image interpretation reports which include the certain image interpretation item and the other includes image interpretation reports which do not include the certain image interpretation item. Here, a description is given of an approach for calculating the correlation ratio between the image interpretation item "Early stain" and the image feature quantity "Average luminance value inside tumor in early phase". In Expression 1, it is assumed that the category i=1 includes the "Early stain", and that the category i=2 does not include the "Early stain". Here, $x_{1j}$ denotes the i-th observed value that is the "Average luminance value inside tumor in early phase" in the tumor image extracted from the case whose image interpretation report(s) include(s) the "Early stain". Here, $x_{2j}$ denotes the j-th observed value that is the "Average luminance value inside tumor in early phase" in the tumor image extracted from the case whose image interpretation report(s) do(es) not include the "Early stain". The "early stain" indicates that a CT value increases in the early phase in the contrast radiography, and thus the correlation ratio is expected to be increased (to a value close to 1) in this case. Furthermore, the early stain depends on the type of the tumor, but does not depend on the size of the tumor, and thus the correlation between the image interpretation item "Early stain" and an image feature quantity "Tumor size" is small (a value close to 0). In this way, the correlations between all the image interpretation items and all the image feature quantities are calculated.

Figure 9:
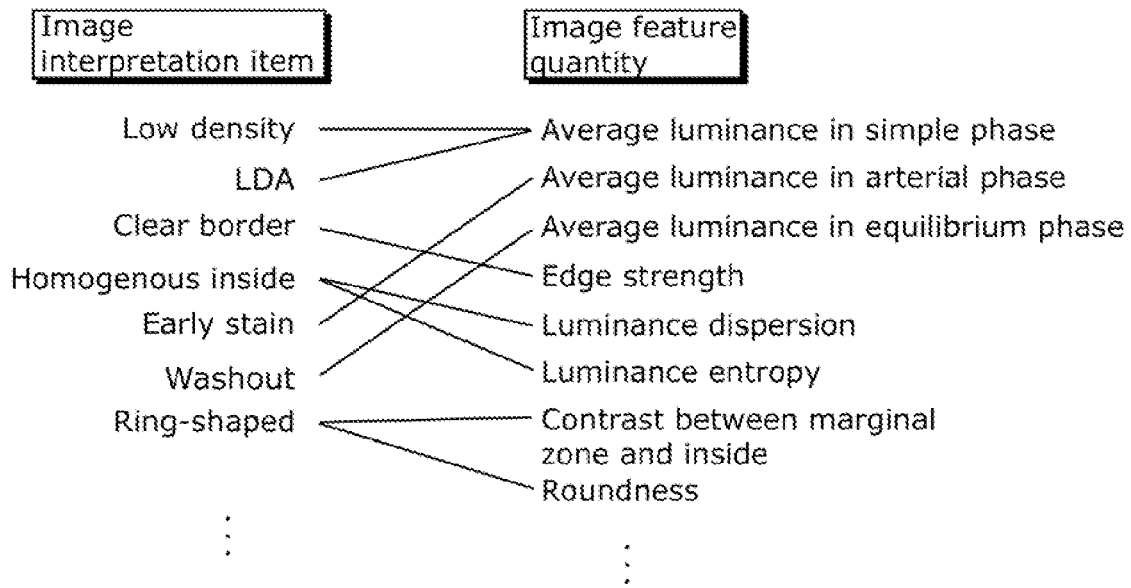
FIG. 9 is a conceptual chart of correlations (in a two-value representation) between image interpretation items and image feature quantities according to Embodiment 1.

FIG. 9 is a conceptual chart of correlations (here, correlation ratios) between image interpretation items and image feature quantities. The image interpretation items are listed at the left side, and the names of the image feature quantities are listed at the right side. Each of pairs of an image interpretation item and an image feature quantity having a correlation value larger than or equal to a threshold value is connected by a solid line. Each of the correlation ratios is any value within a range from 0 to 1 inclusive, and thus any value approximately within a range from 0.3 to 0.7 inclusive can be used as the threshold value. When the calculated correlation ratios are finally binarized based on the threshold value, information as shown in FIG. 9 is obtained. Supplemental information is given for this example. In contrast CT scans for detecting liver tumors, most tumors are drawn in a low density in CT images (that are called as simple images, simple CT images, simple phases, or the like) obtained before the application of contrast media. In most cases, the image interpretation reports of the tumors include any one of descriptions of "Low density", "Low Density Area (LDA) observed", and the like. For this reason, high correlations are observed between the image interpretation items such as "low density" and "LDA" and the average luminance values inside the tumors in the CT images before the application of the contrast media (an example of the average luminance values is shown as an abbreviated version that is "Average luminance in simple phase").

Figure 10:
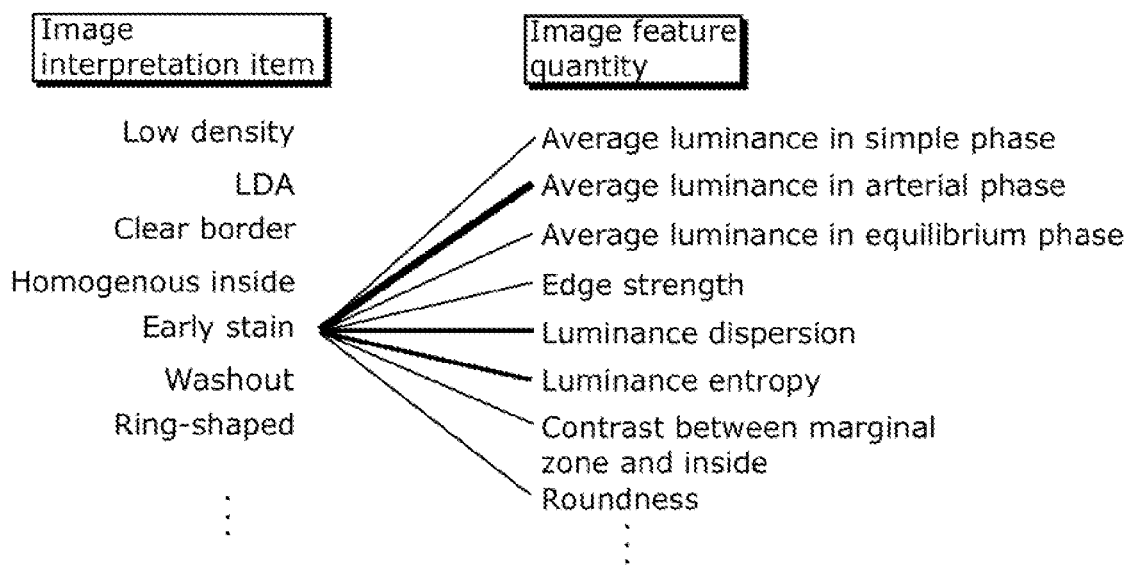
FIG. 10 is a conceptual chart of correlations (in a multi-value representation) between image interpretation items and image feature quantities according to Embodiment 1.

FIG. 10 is a conceptual chart of correlations (here, correlation ratios) between image interpretation items and image feature quantities. In this chart, the correlation ratios between the image interpretation items and the image feature quantities are shown in a multi-value representation in which the boldness of the solid lines corresponds to the magnitudes of the correlation ratios. For example, the highest correlation is observed between the "Early stain" related to the early phase in which the CT value increases in the contrast radiography and the average luminance value inside the tumor (abbreviated as "Average luminance in arterial phase" in FIG. 10) in the early arterial phase (abbreviated as "Early phase" or "Arterial phase").

Focusing on these values of the correlation ratios makes it possible to identify the image feature quantities highly related to the certain image interpretation item. In reality, it is highly likely that one case includes a plurality of lesions (tumors) and for which a plurality of images are captured. The image interpretation report of the case includes descriptions about the lesions. For example, in a contrast CT scan, CT images are captured at plural time points before and after the application of a contrast medium. For this reason, sets of slice images are obtained, each of the sets of slice images includes plural lesions (tumors), and a plurality of image feature quantities are extracted from each of the lesions. For this reason, the number of image feature quantities is obtained according to the Expression (the number of sets of slice images)×(the number of lesions detected from a patient)×(the number of kinds of image feature quantities). In addition, it is necessary to calculate the correlation between (i) each of the image feature quantities and (ii) each of corresponding ones of the image interpretation items and the disease name extracted from the image interpretation report. There is a possibility that such correlations are calculated accurately by using a large number of cases. However, it is possible to calculate the correlations more accurately by associating, in advance, the descriptions in the image interpretation report and the image feature quantities corresponding to the descriptions to some extent based on, for example, the lesion positions and time phases as in FIG. 7.

In the above description, the image interpretation reports are classified into two categories based on the presence/absence of the certain image interpretation item. However, the image interpretation reports are classified into two categories based on the presence/absence of the certain image interpretation item (for example, "Clear border") and the antonym image interpretation item (for example, "Unclear border"). If the image interpretation items are presented in an ordinal scale represented as descriptions "Low density", "Medium density", and "High density", it is possible to calculate the correlation ratios using these descriptions as categories (three categories in this example).

Furthermore, the synonyms such as "Low density", "Low luminance", and "Low absorption" are associated with each other as the identical image interpretation item in a synonym dictionary prepared in advance and handled as such.

(2) Correlation Between Image Feature Quantities and Disease Names

Figure 11:
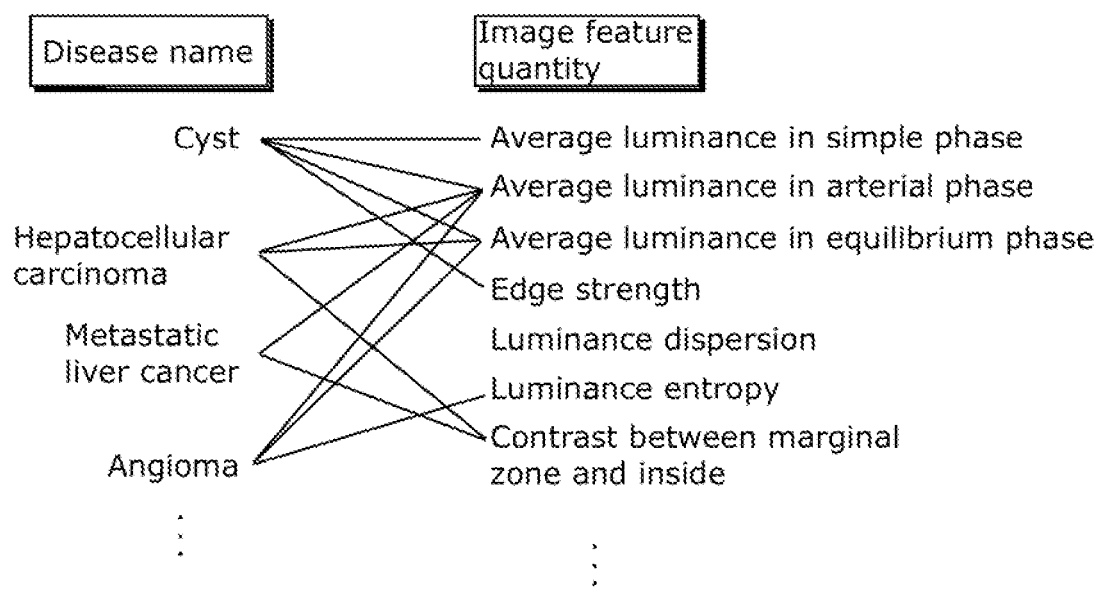
FIG. 11 is a conceptual chart of correlations (in a two-value representation) between disease names and image feature quantities according to Embodiment 1.

Correlation ratios can be used as the correlations between image feature quantities and disease names in pairs, as in the example of the image feature quantities and the image interpretation items in the pairs. FIG. 11 is a conceptual chart of correlations (here, correlation ratios) between the disease names and the image feature quantities. The correlations are shown in a binary representation as in FIG. 9, but it is naturally possible to use a multi-value representation as in FIG. 10.

(3) Correlation Between Image Interpretation Items and Disease Names

A description is given of how to calculate the correlation between an image feature quantity and an image interpretation item in a pair. A log-likelihood ratio is used here from among several kinds of representation forms of correlations. The log-likelihood ratio is an index indicating the strength of co-occurrence between qualitative data items, and represented according to Expression 2.

[Math. 2]

$$G(X, Y) = a\log\frac{aN}{(a+b)(a+c)} + b\log\frac{bN}{(a+b)(b+d)} + c\log\frac{cN}{(a+c)(c+d)} + d\log\frac{dN}{(b+d)(c+d)} \quad \text{(Expression 2)}$$

Here, X denotes an image interpretation item, and Y denotes a disease name.

Each of a, b, c, and d denotes an appearance frequency of a combination of words.

|  | Y | ¬Y | Sum |
|---|---|---|---|
| X | a | b | a + b |
| ¬X | c | d | c + d |
| Sum | a + c | b + d | N | a denotes the co-occurrence frequency of Words X and Y;
b denotes the appearance frequency of Word X;
c denotes the appearance frequency of Word Y; and
d denotes the no-appearance frequency of Words X and Y.

As clear from Expression 2, the log-likelihood ratios can be regarded as co-occurrence indices defined considering Events X and Y, and Exclusive events ¬X and ¬Y.

It is also possible to use, for example, support values shown in Expression 3, confidence values shown in Expression 4, and lift values shown in Expression 5, instead of the log-likelihood ratios. Alternatively, it is also possible to use conviction and phi-coefficients. Conviction values and phi-coefficients are described in documents related to a correlation rule analysis. An example of such documents is Non-patent Literature 9: "Data Mining and its Applications", written by Kato, Hamuro, and Yata, Asakura Publishing Co. Ltd.

[Math. 3]

$$\text{support}(X \Rightarrow Y) = \frac{\text{count}(X \cup Y)}{|D|} \quad \text{(Expression 3)}$$

Here, X and Y are arbitrary item sets (X, Y⊆ I);
|D| is the number of all transactions; and
count (X) is the number of transactions including the item set X in a database D Here, a correlation rule between an image interpretation item and a disease name in each pair is calculated. The definitions of the terms are modified as indicated below.

X denotes one image interpretation item;
$I_1$ of X⊆ $I_1$ denotes the item set related to an image interpretation item;
Y denotes one disease name;
$I_2$ of Y⊆ $I_2$ denotes the item set related to a disease name;
|D| denotes the number of all transactions; and
count (X∪Y) is the number of cases whose image interpretation reports include both of the image interpretation item X and the disease name Y.

Each of these support values means the probability (co-occurrence probability) of the co-occurrence of the interpretation item X and the disease name Y in each of the cases. When the interpretation item X and the disease name Y simultaneously appear in most of the interpretation reports of the cases, the interpretation item X and the disease name Y are regarded as having a high correlation.

[Math. 4]

$$\text{confidence}(X \Rightarrow Y) = \frac{\text{count}(X \cup Y)}{\text{count}(X)} = P(Y|X) \quad \text{(Expression 4)}$$

Here, X and Y are arbitrary item sets (X, Y⊆ I); and
count (X) is the number of transactions including the item set X in the database D.

Each of these confidence values means the probability of the appearance of the conclusion portion Y under the condition that the item of the condition portion X appears. When the disease name Y appears in any of the interpretation reports in which the image interpretation item X appears, the interpretation item X and the disease name Y are regarded as having a high correlation.

[Math. 5]

$$\text{lift}(X \Rightarrow Y) = \frac{\text{confidence}(X \Rightarrow Y)}{P(Y)} = \frac{P(Y|X)}{P(Y)} \quad \text{(Expression 5)}$$

Here, X and Y are arbitrary item sets (X, Y⊆ I); and
count (X) is the number of transactions including the item set X in the database D;
P (Y) denotes the appearance probability of the item set Y; and $$P(Y) = \frac{\text{count}(Y)}{|D|}$$

|D| denotes the number of all transactions.

Each of the lift values is an index showing how much the appearance probability (that is the confidence value) of the disease name Y under the condition that the image interpretation item X appears, with respect to the appearance probability of the disease name Y without the condition that the image interpretation item X appears. When the lift value is 1.0, the appearance probability of the disease name Y does not change even when the image interpretation item X does not appear, and thus the rule is of interest (this rule is "the image interpretation item X⇒ the disease name Y" which means that the disease name is Y when the image interpretation item is X). This means that the appearance of the image interpretation item X and the appearance of the disease name Y are statistically independent of each other. The rule is regarded as being of higher interest as the lift value is more higher than 1.0. In other words, the correlation between the image interpretation item X and the disease name Y is regarded as being higher.

Figure 12:
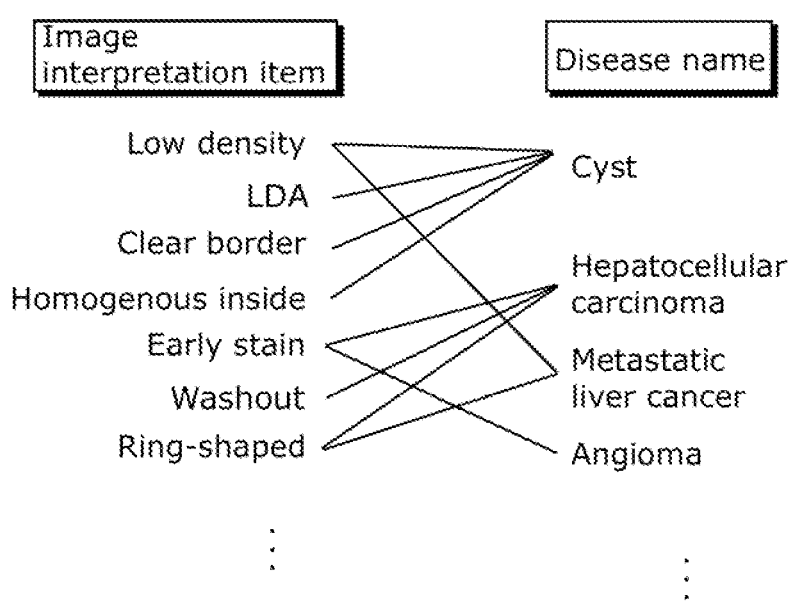
FIG. 12 is a conceptual chart of correlations (in a two-value representation) between image interpretation items and disease names according to Embodiment 1.

FIG. 12 shows a conceptual chart of correlations (for example, log-likelihood ratios) between image interpretation items and disease names. The correlations are shown in a binary representation as in FIG. 9, but it is naturally possible to use a multi-value representation as in FIG. 10.

When performing Step S14 according to the aforementioned approach, the following are respectively obtained: the correlations between image feature quantities and image interpretation items as in FIG. 13; the correlations between image feature quantities and disease names as in FIG. 14; and the correlations between image interpretation items and disease names as in FIG. 15. The numerical values in the table are correlation ratios in FIG. 13 and FIG. 14, and are log-likelihood ratios in FIG. 15. The correlation ratios are values in the range from 0 to 1 inclusive. The log-likelihood ratios are any values larger than or equal to 0. In addition, the obtained correlations are stored in the image interpretation knowledge database 110 in the forms of FIG. 13, FIG. 14, and FIG. 15.

(Similar Case Search)

Hereinafter, a description is given of a procedure of a search for a similar case using the flowchart of FIG. 16 and an example of an image screen for a similar case search in FIG. 17. The exemplary image screen for a similar case search shown in FIG. 17 is presented on a display device when the single display device functions as both the report input and output unit 140 and the display unit of the similar case display unit 190.

In Step S20, the interpretation target image reading unit 120 obtains the interpretation target image from the medical image capturing apparatus. As in the generation of image interpretation knowledge in FIG. 2, the medical image capturing apparatus that is the target in this embodiment is a multi-slice CT apparatus, and the target organ and disease is a liver tumor. The read image (the target image 201 in FIG. 17) is displayed on the interpretation target image display unit 130.

In Step S21, the user inputs the image interpretation report through the report input and output unit 140 with reference to the interpretation target image displayed on the interpretation target image display unit 130. The input image interpretation reports are displayed on the image interpretation report input and output area 210 in FIG. 17. In the case of the multi-slice CT apparatus, a plurality of slice images along a vertical surface (the axial view) with respect to the body axis are normally obtained through reconfiguration of the images. The user checks whether or not a lesion (a liver tumor in this embodiment) is present or absent while changing the slice positions on these slice images, and input descriptions in the interpretation report. When inputting descriptions in the interpretation report, the position (the slice number and the coordinate on the slice image or area information) of the lesion detected in the interpretation target image may be specified by the user using an input device such as a mouse. When there is a plurality of lesions in the interpretation target image and a plurality of descriptions is input in the image interpretation report, it is good to clearly record the associations between the lesions in the interpretation target image and the descriptions. Such clear indications of the associations are useful when generating an image interpretation knowledge database 110 using the image interpretation report.

Figure 18:
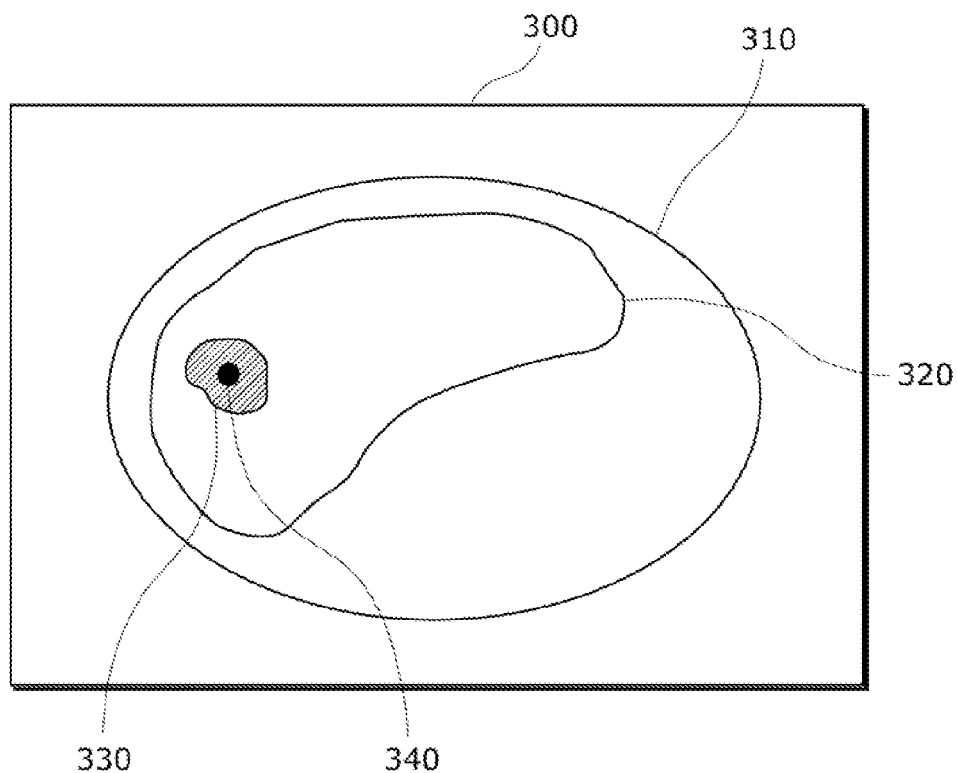
FIG. 18 is an illustration of a specification of a lesion position or a lesion area according to Embodiment 1.

FIG. 18 illustrates a specification of a lesion position or a lesion area. An interpretation target image 300 (an abdominal CT image here) shown in FIG. 18 includes a surrounding area 310 in an abdominal part, a target organ (a liver here) 320, and a lesion area 330. When a coordinate is specified, for example, an approximately center position (a point 340 in FIG. 18) of the tumor is clicked using a mouse. Examples of schemes to specify an area include, a scheme for enclosing the lesion area 330 in FIG. 18 by a rectangle, a circle, or an oval circle, and a scheme for specifying a boundary between the lesion portion (the lesion area 330 in FIG. 18) and a normal organization (the outside of the lesion area 330) using a free-form curve. The scheme for specifying only the center coordinate or specifying the area by enclosing the area by the rectangle, the circle, or the over circle has an advantage of placing a small burden on the user, but requires that the accurate lesion area is automatically extracted using an image processing algorithm for an image feature quantity extraction. As for a tumor area extraction, the same approach as in Step S112 can be used.

In Step S22, a user's request for a similar case search is received.

In the case of a tumor having a typical symptom or a skilled doctor, inputs in the image interpretation report are normally completed without difficulty in the diagnosis. However, in the case of a tumor having a non-typical symptom or a fresh doctor, the doctor makes a request for a similar case search using the image interpreting terminal 200. The request for a similar case search is performed, for example, by clicking a similar case search icon 220 in FIG. 17. When a plurality of lesions is present in the interpretation target image, the lesion difficult to diagnose is specified, and then such a request for a similar case search is performed.

How to specify these lesions is described. When a plurality of positions or areas of the lesions including the lesion difficult to diagnose is already specified before inputs in the image interpretation report in Step S21, it is only necessary that one of these positions or areas is selected. When the lesion difficult to diagnose is not yet specified in Step S21, the lesion is newly specified here. As the specification scheme, it is possible to specify one point around the center of the lesion, or to specify the lesion area. As for the specification of the point or the area, it is possible to use the same scheme as in Step S21. When the one point around the center is specified, a detailed lesion area is set using the same scheme as in Step S112 from a proximity area with respect to the specified point. When the lesion area is roughly specified, the detailed lesion area is specified in the roughly-specified lesion area using the same scheme as in Step S112.

When such a doctor's request for a similar case search is made, a transition to Step S23 is made. At this time, input of descriptions in the interpretation report may be completed, or may be in progress. The similar case search in Step S25 can be executed even when no descriptions is input in the interpretation report. In this case, the similar case search is executed using a pre-set reference set of image features without executing a similar case search according to a doctor focus point that is a feature of the present disclosure.

Figure 16:
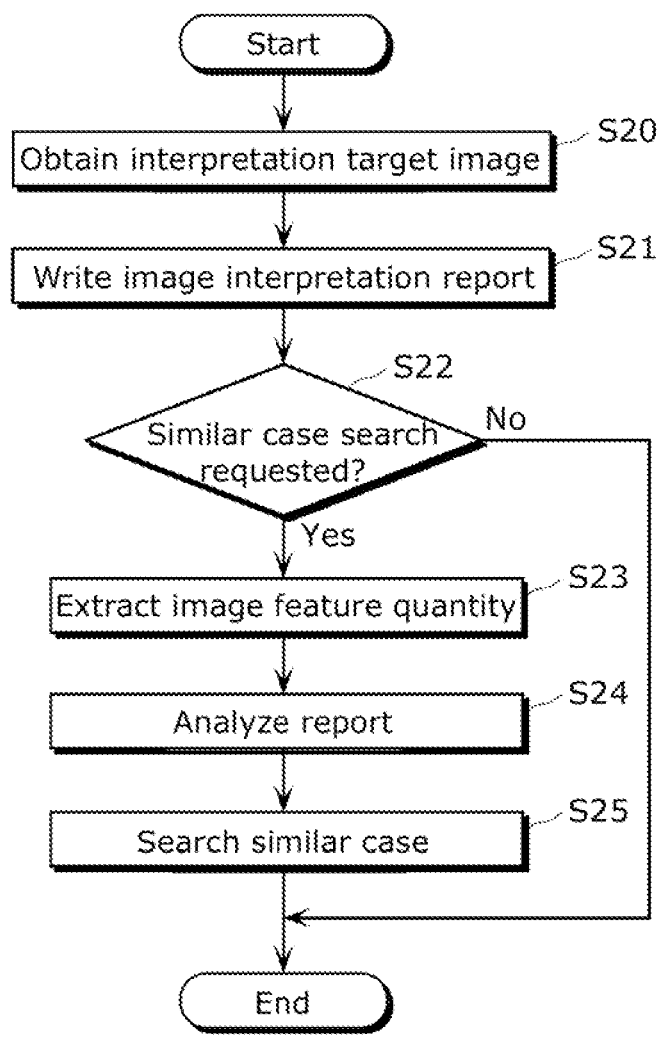
FIG. 16 is a flowchart of a procedure for searching a similar case according to Embodiment 1.
Figure 17:
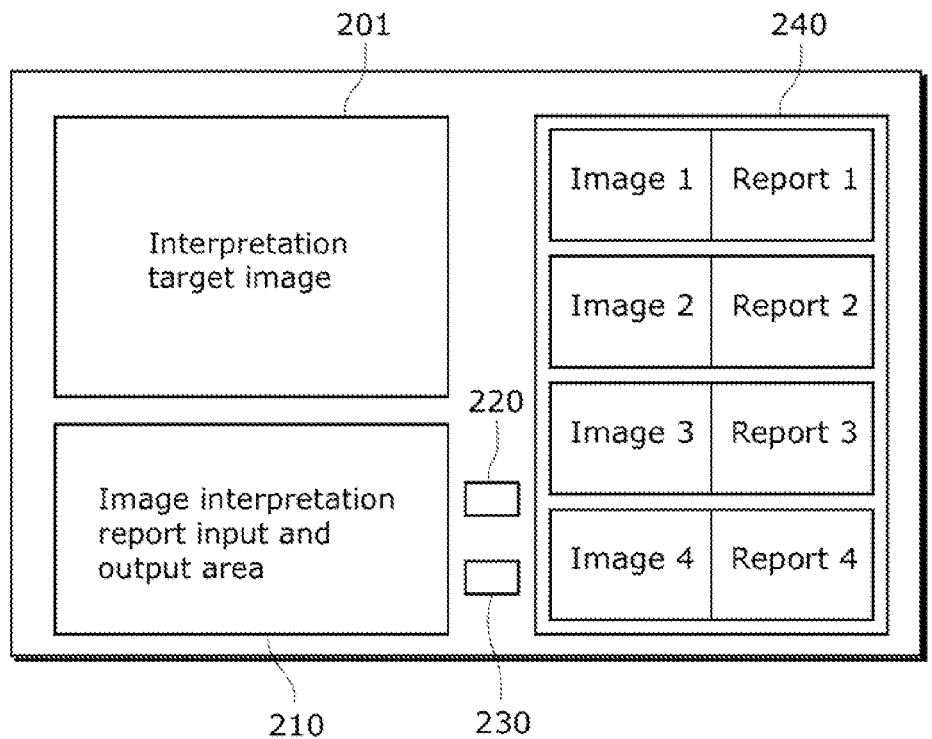
FIG. 17 is an illustration of an example of a display screen for a similar case search according to Embodiment 1.

When an image interpretation report input time lasts over a predetermined time or when an input for terminating the image interpretation report input time is made, the process in FIG. 16 is completed. The processing unit for receiving the similar case search request and the image interpretation termination input is not shown in FIG. 1. The processing unit may be a physical switch embedded in the keyboard or the like in the image interpreting terminal 200, or a GUI menu or the like displayed on the interpretation target image display unit 130 composed of a medical high-definition monitor or the like. FIG. 17 is an example of such a GUI menu, the similar case search icon 220 is a virtual bottom for receiving the similar case search request, and the icon 230 is a virtual bottom for receiving the image interpretation termination input.

In Step S23, the image feature quantity extracting unit 160 extracts image feature quantities from each of the lesion areas specified or extracted in the interpretation target image in Step S22. When plural lesion areas are specified or extracted, a predefined $N_F$ number of feature quantities are extracted for each of the lesion areas. The scheme for extracting the image feature quantities is the same as in Step S114.

In Step S24, the report analyzing unit 150 analyzes the image interpretation report including the descriptions input in Step S21. Here, the process performed here is the same as the extraction of the image interpretation items and the disease name in Step S12 in the generation of the image interpretation knowledge database.

In Step S25, the weight determining unit 170 and the similar case search unit 180 search the case database for similar cases, based on the interpretation target image and the image interpretation report including the descriptions input by the doctor. The searched-out similar cases are displayed in a similar case output area 240 in FIG. 17. States considered here are as follows: the state in which the image interpretation report in FIG. 4 is already written by the doctor in Step S21; the state in which the image interpretation items and the disease name in FIG. 5 are already extracted in FIG. 24; and the state in which the image feature quantities are already extracted from the interpretation target image in Step S23. In addition, the image interpretation knowledge database 110 already stores the correlations between two of three data types that are the image feature quantity, the image interpretation item, the disease name as shown in FIG. 13, FIG. 14 and FIG. 15.

In this embodiment, weighted distance calculations are performed in the similar case search, based on at least one of the image interpretation items and disease name extracted from the image interpretation report. In other words, comparatively large weights are added to the image feature quantities related to the extracted at least one of the image interpretation items and disease names, and comparatively small weights are added to the image feature quantities not related to the same. In this way, it is possible to perform a similar case search reflecting the doctor focus point input in the image interpretation report. In other words, the similar case search unit 180 calculates the weighted distances between each of the medical images stored in the case database 100 and the interpretation target image. The similar case search unit 180 searches out, from the case database 100, the similar case that is the case including the medical image used to perform a weighted distance calculation that yields a value smaller than a predetermined threshold value. Alternatively, the similar case search unit 180 searches out, from the case database 100, the similar case that is the case including medical images used to perform weighted distance calculations that yield a predetermined number of weighted distance values selected in the descending order of smallness.

Each of the weighted distances can be calculated, for example, according to Expression 6.

[Math. 6]

$$D_W(x, u^i) = \sqrt{\sum_{j=1}^{n} w_j(x_j - u^i_j)^2} .$$ (Expression 6)

x denotes an unknown vector;
$u^i$ denotes an i-th vector among comparison targets;
n denotes the number of dimensions of a vector; and
$w_j$ denotes a weight on the j-th dimension.

Here, x denotes a vector to which all the ($N_F$ number of) image feature quantities extracted from the interpretation target image are connected. In addition, $u^i$ denotes an image feature quantity extracted from the i-th case among the cases stored in the case database 100. When connecting different kinds of image feature quantities, canonicalization (normalization to average 0 and disperse 1) is performed in advance so as not to affect the difference in the scales of the feature quantities.

A specific example of a weighting scheme is described below.

(1) Case where Both Image Interpretation Items and Disease Name are Extracted from Image Interpretation Report This case corresponds to a state in which the doctor completes most of the inputs in the image interpretation report, and tries to confirm the inputs based on a result of a similar case search.

The example described here relates to the case of adding weights utilizing all the correlations between the image interpretation items and the image feature quantities and all the correlations between the image interpretation items and the disease names. The former shows correspondence between technical image feature quantities and medical image interpretation items (that are "determined by doctors from a medical perspective", and thus each of the correlations gives a medical meaning to the corresponding image feature quantities. The latter shows the correspondence between the image interpretation items determined by the doctors from a medical perspective and the disease name (determined based on a combination of the image interpretation items), and thus each of the correlations is based on the diagnosis-related knowledge of the doctors. When using both the two types of correlations according to the latter scheme, it is possible to perform a similar case search considering the both. More specifically, when a plurality of image interpretation items are already input in the image interpretation report, it is possible to synthesize the weights between the image interpretation items and the image feature quantities according to the degrees of influence of the respective image interpretation items in the determination of the disease.

The correlations between the disease names and the image feature quantities can also be used, but these correlations are not used here for the following reasons. When a disease has a plurality of symptoms (for example, three types of A, B, and C), image feature quantities related to the symptom A and image feature quantities related to the symptom B are different from each other. When determining the weights of the image feature quantities from the disease name, the mixed (averaged) weights of the image feature quantities of the symptoms A, B, and C are used. Most of the cases related to the image interpretation items are already identified, it is possible to perform a similar case search according to the doctor focus points using image interpretation items.

At this time, "Early stain" and "Washout" are extracted as the image interpretation items, and "Hepatocellular carcinoma" is extracted as the disease name as shown in FIG. 5 from the image interpretation report in FIG. 4. The weight determining unit 170 obtains the correlation between the early stain and the hepatocellular carcinoma and the correlation between the washout and the hepatocellular carcinoma, with reference to the correlation table between the image interpretation items and the disease names stored in the form of the table of FIG. 15 in the image interpretation knowledge database 110. Here, the raw numerical values indicating the obtained correlations are used as weights, and are respectively denoted as $w_x$ and $w_y$. In addition, the weight determining unit 170 obtains the correlations between "Early stain" and the respective image feature quantities and the correlations between "Washout" and the respective image feature quantities, with reference to the correlation table between the image feature quantities and the image interpretation items stored in the form of the table of FIG. 13 in the image interpretation knowledge database 110. Here, the raw numerical values indicating the obtained correlations are used as weights, and are respectively denoted as $w_{a,i}$ and $w_{b,i}$. Here, i is a subscript showing the type of the image feature quantity. The weight determining unit 170 calculates the weight $W_i$ corresponding to the i-th image feature quantity using these weights according to Expression 7.

[Math. 7]

$$W_i = w_x w_{a,i} + w_y w_{b,i} \quad \text{(Expression 7)}$$

Figure 19:
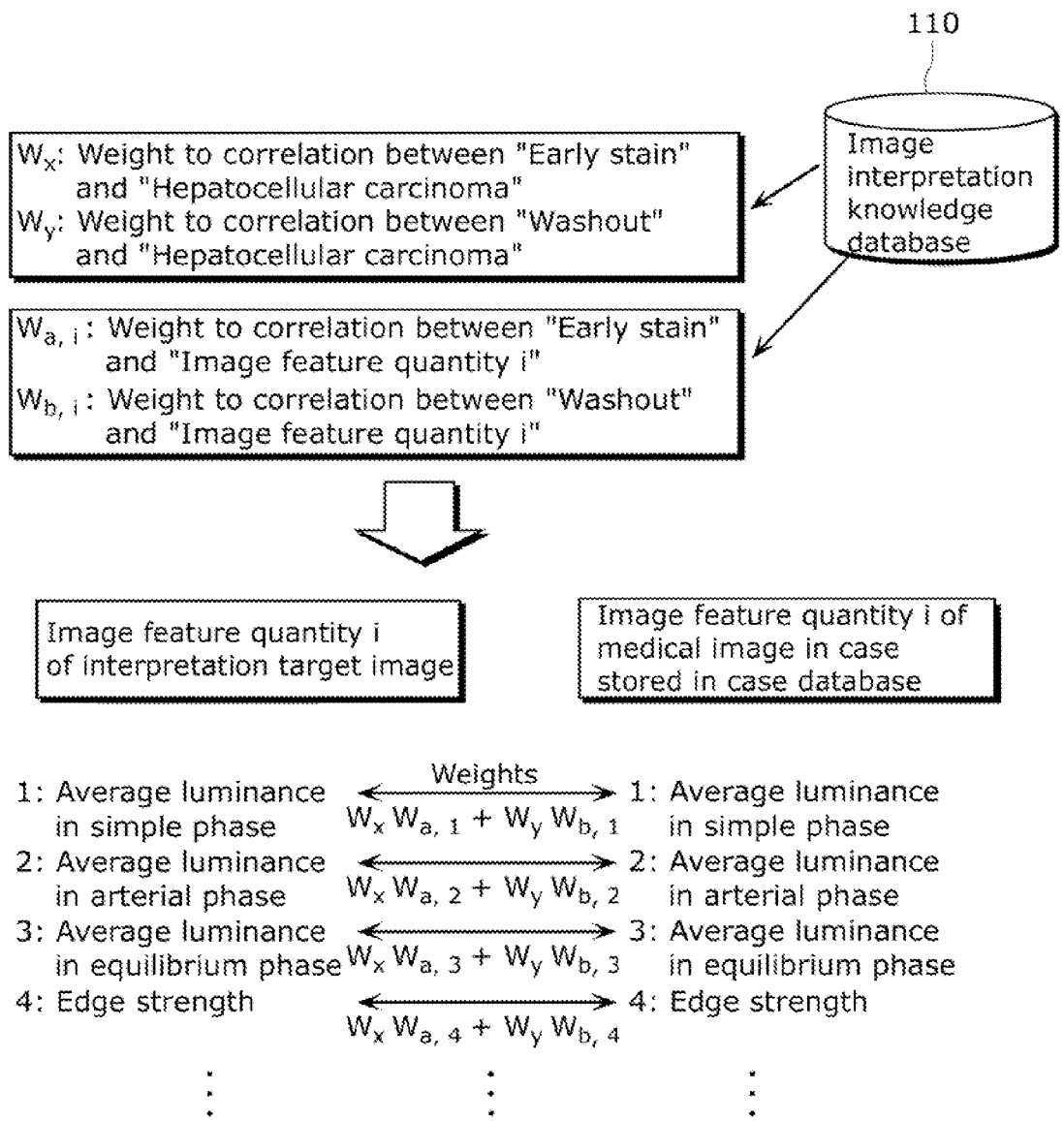
FIG. 19 is an illustration of a weighting scheme 1 in a search for a similar case according to Embodiment 1.

FIG. 19 shows the outline of the weighting scheme described above.

For example, the weight to a fourth image feature quantity "Edge strength" is calculated as a sum of $w_x w_{a,4}$ and $w_y w_{b,4}$. Here, $w_x w_{a,4}$ is a value obtained by weighting the value $w_{a,4}$ indicating the correlation between the early stain and the edge strength using the value $w_x$ indicating the correlation between the early stain and the hepatocellular carcinoma related to the same image interpretation item. Here, $w_y w_{b,4}$ is a value obtained by weighting the value $w_{b,4}$ indicating the correlation between the washout and the edge strength using the value $w_y$ indicating the correlation between the washout and the hepatocellular carcinoma related to the same image interpretation item.

When the number of the image interpretation items is other than 2, it is possible to calculate such a value by adding the correlation between the image interpretation item and the image feature quantity weighted with the value indicating the correlation between the image interpretation item and the disease name. According to this Expression, it is possible to calculate weights considering the image interpretation item focused by the doctor and the disease name, the correlation between each of the image interpretation items and the disease name, and the correlation between each of the image interpretation items and each of the image feature quantities. As a result, it is possible to perform a similar case search based heavily on the weighted information. More specifically, when a plurality of image interpretation items are already input in the image interpretation report, it is possible to synthesize the weights between the image interpretation items and the image feature quantities according to the degrees of influence of the respective image interpretation items in the determination of the disease.

In the flowchart of FIG. 16, a similar case search is executed only when a similar case search request is made. However, it is also good to execute a similar case search at another timing during the input in the image interpretation report. An example of such another timing is employed in the case where no input is made in the image interpretation report over a certain time period after at least one image interpretation item or disease name is input. Assuming that the doctor has difficulty in interpreting the image, an operation approach is taken with an aim to accelerate the interpretation by presenting a similar case as a hint. In this embodiment, when the at least one image interpretation item or disease name is input, it is possible to execute a similar case search based on the doctor focus point. Hereinafter, descriptions are given of also a case where only the image interpretation item is extracted from the image interpretation report and a case where only the disease name is extracted from the same.

(2) Case where Only Image Interpretation Item can be Extracted from Image Interpretation Report.

This case corresponds to a state in which the doctor can determine one or more interpretation items that should be focused on to diagnose a disease, but has difficulty in making a final diagnosis of the disease, and thus is trying to get a hint for diagnosing the disease based on a result of a similar case search. Here, weighting is performed based only on all the correlations between image interpretation items and image feature quantities.

At this time point, it is assumed that the "Early stain" and "Washout" are extracted as the image interpretation items in the image interpretation report (not shown). The weight determining unit 170 obtains the correlations between "Early stain" and the respective image feature quantities and the correlations between "Washout" and the respective image feature quantities, with reference to the correlation table between the image feature quantities and the image interpretation items stored in the form of the table of FIG. 13 in the image interpretation knowledge database 110. Here, the raw numerical values indicating the obtained correlations are used as weights, and are respectively denoted as $w_{a,i}$ and $w_{b,i}$. Here, i is a subscript showing the type of the image feature quantity. The weight determining unit 170 calculates the weight $w_i$ corresponding to the i-th image feature quantity using these weights according to Expression 8.

[Math. 8]

$$W_i = w_{a,i} + w_{b,i} \quad \text{(Expression 8)}$$

Figure 20:
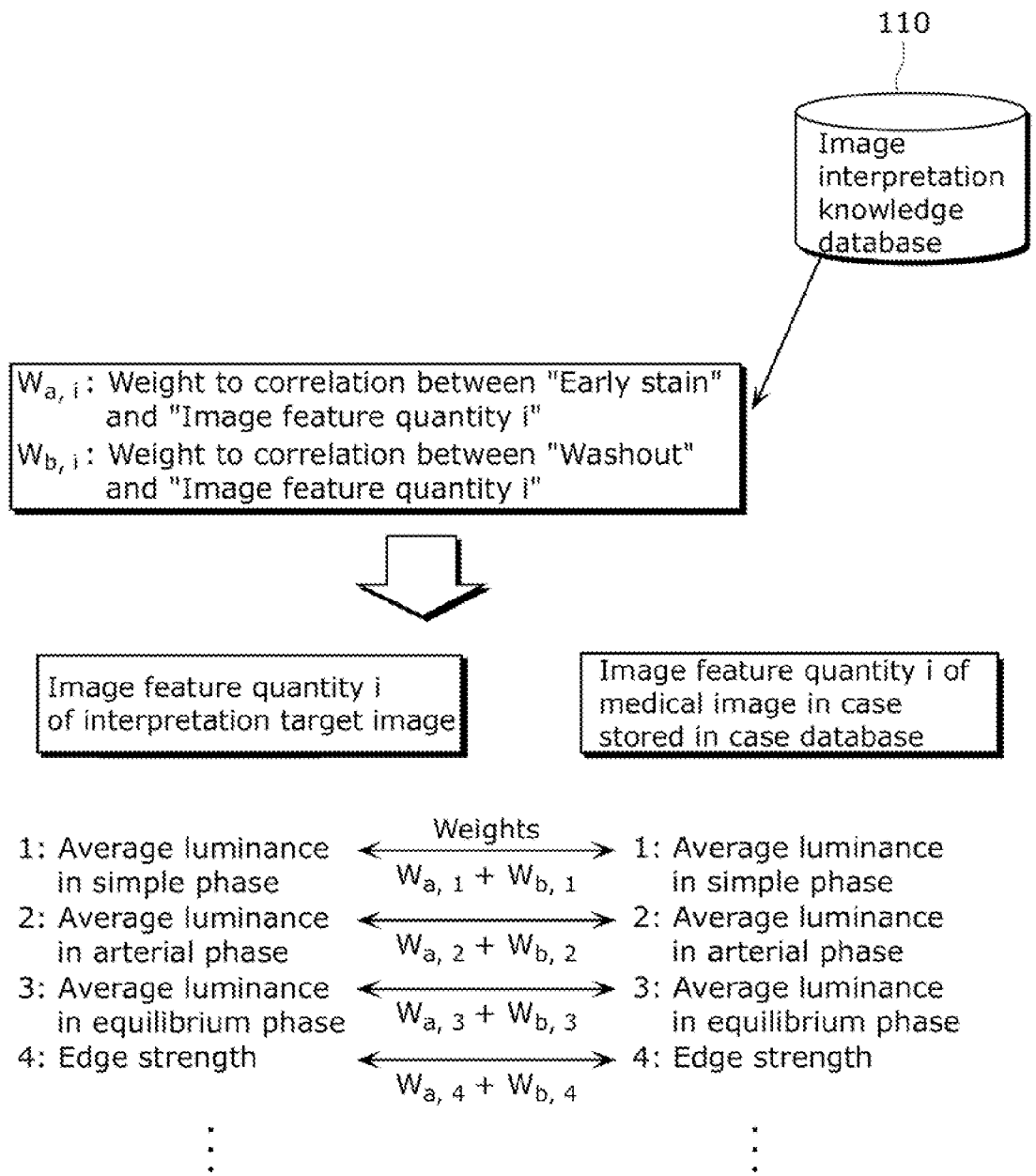
FIG. 20 is an illustration of a weighting scheme 2 in a search for a similar case according to Embodiment 1.

FIG. 20 shows the outline of the weighting scheme described above.

For example, the weight to the fourth image feature quantity "Edge strength" is a value obtained by adding the value $w_{a,4}$ indicating the correlation between the early stain and the edge strength and the value $w_{b,4}$ indicating the correlation between the washout and the edge strength.

When the number of the image interpretation items is other than 2, it is possible to calculate such a value by adding the correlation between the image interpretation item and the image feature quantity. According to this Expression, it is possible to calculate a weight considering the image interpretation item focused by the doctor, and the correlation between each of the image interpretation items and each of the image feature quantities. As a result, it is possible to perform a similar case search based heavily on the weighted information. However, when plural image interpretation items are extracted, these image interpretation items are handled evenly without being prioritized. However, if it is possible to newly input an estimated disease name in the image interpretation report using, as a hint, a case obtained as a result of a similar case search based only on image interpretation items, it is possible to synthesize the weights between the image interpretation items and the image feature quantities according to the degrees of influence of the image interpretation items in the determination of the disease name as described in the Item (1) Case where Both Image Interpretation Items and Disease Name Are Extracted from Image Interpretation Report.

(3) Case where Only Disease Name can be Extracted from Image Interpretation Report This case corresponds to a state in which the doctor can estimate the disease name based on his or her intuition and the like, but has difficulty in determining image interpretation items that are the bases of the estimation, and thus is trying to get a hint for the bases (image interpretation items) of the diagnosis based on the result of the similar case search. Here, weighting is performed based only on the correlations between the disease name and the respective image feature quantities.

At this time point, it is assumed that "Hepatocellular carcinoma" is extracted as the disease name in the image interpretation report. The weight determining unit 170 obtains the correlations between the "Hepatocellular carcinoma" and the respective image feature quantities with reference to the correlation table between the image feature quantities and the disease name stored in the form of the table of FIG. 14 in the image interpretation knowledge database 110. Here, the raw numerical values indicating the correlations are used as weights, and are denoted as $w_i$. Here, is a subscript showing the type of the image feature quantity. The weight determining unit 170 calculates the weight $W_i$ corresponding to the i-th image feature quantity using these weights according to Expression 9.

[Math. 9]

$$W_i = w_i \quad \text{(Expression 9)}$$

Figure 21:
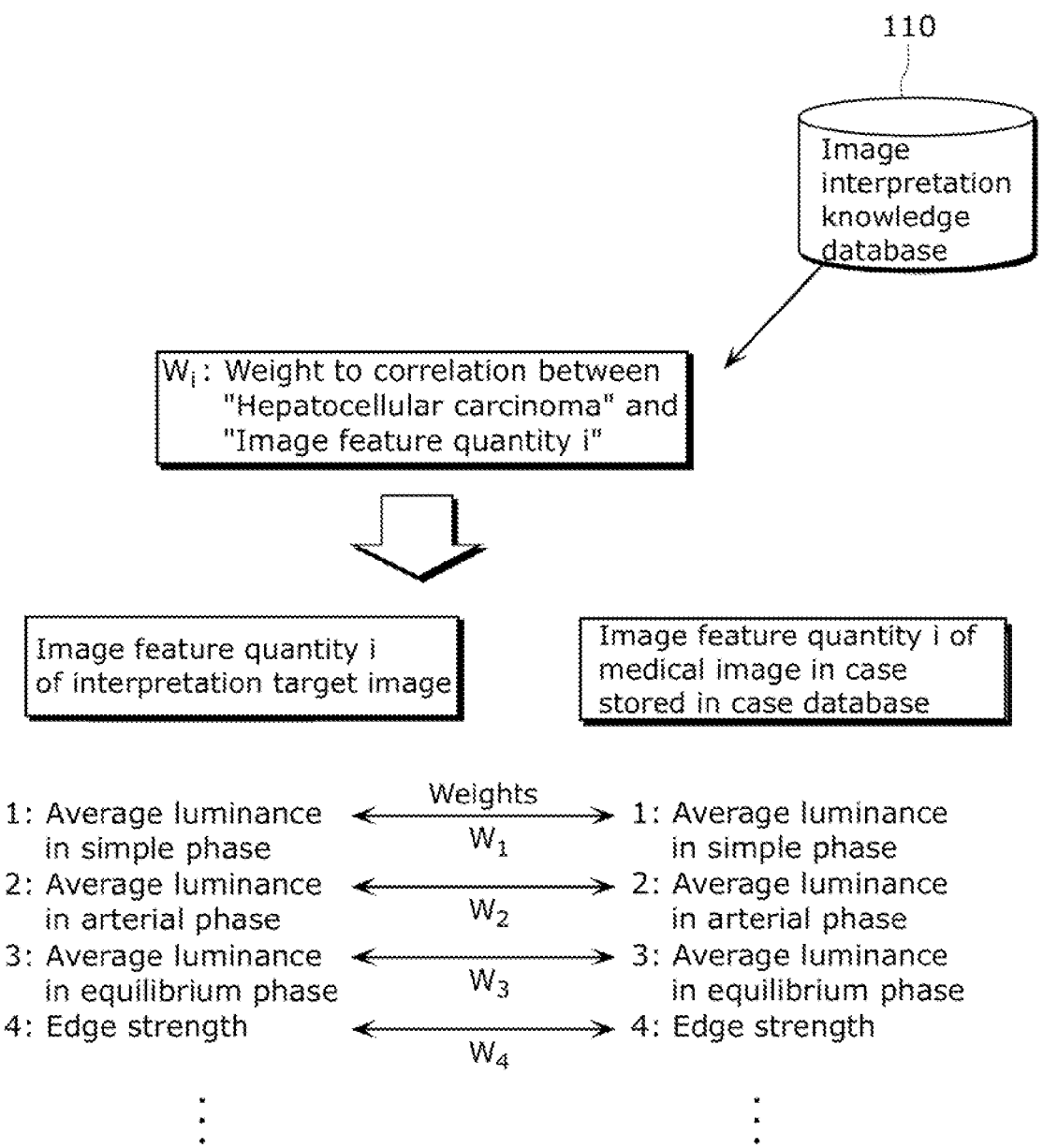
FIG. 21 is an illustration of a weighting scheme 3 in a search for a similar case according to Embodiment 1.

FIG. 21 shows the outline of the weighting scheme described above.

For example, the weight to the fourth image feature quantity "Edge strength" is the value $w_a$ indicating the correlation between the hepatocellular carcinoma and the edge strength.

The disease name is normally one, and thus it is only necessary to perform the aforementioned processes. However, when two or more disease names are input, it is possible to perform a similar case search that provides the same effect by adding the weights in the processes. Adding the weights makes it possible to search for a similar case based on the averaged image feature quantity related to the two or more diseases. According to this Expression, it is possible to calculate weights considering image interpretation items focused by the doctor, and the correlations between each of the image interpretation items and each of the image feature quantities. As a result, it is possible to perform a similar case search based heavily on the weighted information. However, if it is possible to newly input an estimated image interpretation item in the image interpretation report using, as a hint, a case obtained as a result of a similar case search based only on a disease name, it is possible to calculate weights considering image interpretation items focused by the doctor and the disease name, the correlation between each of the image interpretation items and the disease name, and the correlation between each of the image interpretation items and each of the image feature quantities, and as a result, it is possible to perform a similar case search based heavily on the weighted information, as described in the Item (1) Case where Both Image Interpretation Items and Disease. Name Are Extracted from Image Interpretation Report.

In this embodiment, a determination on the similarity between images is made using a weighted distance according to Expression 6. However, as the number of dimensions of feature quantities for use increases, some of feature quantities having a large correlation ratio may be embedded among a large number of feature quantities having a small (or a medium) correlation ratio in the calculated distances. In this case, it is also good to use, in distance calculations, only image feature quantities having a correlation ratio larger than or equal to a predetermined threshold value or only several image feature quantities having correlation ratios in a top range. The number of the top-range correlation ratios in such a case may be determined in advance.

In the similar case search according to this embodiment, weighted distance calculations are performed in the similar case search, based on at least one of the image interpretation items and disease name extracted from the image interpretation report. In other words, comparatively large weights are added to the image feature quantities related to the extracted at least one of the image interpretation items and disease names, and comparatively small weights are added to the image feature quantities not related to the same. In this way, it is possible to perform a similar case search reflecting the doctor focus points input in the image interpretation report.

Here, a description is given of how to selectively use the three types of weighting schemes.

The weighting scheme in FIG. 19 is used when both of the image interpretation items and the disease name are already input in the image interpretation report, the weighting scheme in FIG. 20 is used when only the image interpretation items are already input in the image interpretation report, and the weighting scheme in FIG. 21 is used when only the disease name is already input in the image interpretation report. It is possible to add a lacking disease name and lacking image interpretation items in the image interpretation report with reference to the similar case obtained as a result of a similar case search according to the scheme of FIG. 20 or FIG. 21. At this stage, it is possible to use the weighting scheme in FIG. 19. This increases the accuracy in the similar case search, and enables reference to a more similar search result, and thereby enables update of the image interpretation report. In this way, it is possible to increase a diagnosis accuracy by performing a search each time any of image interpretation report is updated by utilizing the present disclosure.

Embodiment 2

Embodiment 1 describes image searches (similar case searches) reflecting focus points in image interpretation descriptions written by doctors in image interpretation reports. In the case of a fresh doctor who does not have much experience, descriptions (especially focus points) written in an image interpretation report may be inappropriate. In this case, an image search reflecting the inappropriate focus points is inevitably performed. However, even in this case, there is no possibility that a totally different case is searched out because a similar image search is executed (from another viewpoint) based on image feature quantities obtained from the target image although these image feature quantities are not the image feature quantities that should be focused on. The problem is that an inappropriate image interpretation report is generated, rather than the result of the similar case search. This embodiment illustrates operations performed by a similar case searching apparatus to prevent this problem.

The similar case searching apparatus according to Embodiment 2 of the present disclosure is configured to be basically similar to the similar case searching apparatus shown in FIG. 1 according to Embodiment 1. The same structural elements as in Embodiment 1 are not described here.

The image interpretation knowledge database 110 stores image interpretation knowledge obtained in advance by analyzing a plurality of cases. The contents of the image interpretation knowledge to be stored are slightly different from those in Embodiment 1, and the contents are described in detail later. A weight determining unit 170 determines the validity of each of text feature quantities extracted by a report analyzing unit 150, based on the text feature quantities extracted by the report analyzing unit 150, image feature quantities extracted by an image feature quantity extracting unit 160, and the image interpretation knowledge stored in the image interpretation knowledge database 110, and determines weights to the respective image feature quantities to be used in image searches.

Hereinafter, descriptions are given of operations performed by units according to Embodiment 2 of the present disclosure.

(Preparation of Image Interpretation Knowledge Database)

Prior to a similar case search, image interpretation knowledge is obtained in advance, and is stored in the image interpretation knowledge database 110. The image interpretation knowledge is generated to include a plurality of "cases" each of which is composed of medical images and the image interpretation report that is obtained as a result of interpretation of the medical images. The similar case to be searched out and used here may be a case stored in the case database 100 storing cases and used to search for a similar case, or a case stored in another database. The number of cases required is the number that is sufficient to obtain a certain law and knowledge using various kinds of data mining algorithms. The number of data items is normally any number in a range from several hundreds to several tens of thousands. The image interpretation knowledge used in this embodiment includes: correlations between two of three data types that are (i) the image feature quantity, (ii) the image interpretation item, and (iii) the disease name; and a distribution of image feature quantities of at least one kind corresponding to an image interpretation item or a disease name.

Hereinafter, a procedure for generating the image interpretation knowledge is described with reference to the flowchart of FIG. 2. As in Embodiment 1, it is assumed that the medical image capturing apparatus that is used in this embodiment is a multi-slice CT apparatus, and that a target organ and a target disease are a liver and a liver tumor, respectively.

The operations performed in Step S10 to Step S13 are the same as those in Embodiment 1. At the time point at which Step S14 is reached, for example, a set of data items shown in FIG. 8 is obtained.

In Step S14, image interpretation knowledge is extracted from the image feature quantities obtained in Step S11 and the image interpretation items and the disease name obtained in Step S12. The correlations between two data types in the image interpretation knowledge are the same as in Embodiment 1, and thus the description thereof is not repeated here. As for the distribution of the values of image feature quantities, the following describes a case where the image interpretation knowledge includes the distribution of the values of image feature quantities of "one kind" corresponding to an image interpretation item or a disease name.

(1) Distribution of Image Feature Quantities Corresponding to Image Interpretation Item In FIG. 22, the graph (a) shows the distribution of the values indicating the image feature quantity "Edge strength" observed in images of liver tumors respectively associated in cases with image interpretation reports each of which includes the image interpretation item "Clear border", and the graph (b) shows the distribution of the values indicating the image feature quantity "Edge strength" observed in images of liver tumors respectively associated in cases with image interpretation reports none of which includes the image interpretation item "Clear border". The image feature quantity "Edge strength" is assumed to be a value corresponding to a first-order difference in luminance on a border edge between a tumor (lesion) area and a normal organization area. As for such a case whose image interpretation report includes "Clear border", it is highly likely that the edge strengths at the tumor borders are large, and thus a deviated distribution such as the distribution in the graph (a) of FIG. 22 is obtained. On the other hand, when a large edge strength does not contribute to a diagnosis of a disease, it is highly likely that "Clear border" is not written in the image interpretation reports. For this reason, the graph (b) of FIG. 22 is not deviated than the graph (a) of FIG. 22. In general, the number of cases whose image interpretation reports do not include a given image interpretation item is larger than the number of cases whose image interpretation reports include the given image interpretation item. Thus, the total sum (the integrated value) of frequencies in the graph (b) of FIG. 22 tends to be larger than the total sum (the integrated value) of frequencies in the graph (a) of FIG. 22.

In view of this, the distributions of the image feature quantities extracted from tumor images included in the cases whose image interpretation reports include the given image interpretation item (or the disease name) are newly included in the image interpretation knowledge and used in this embodiment. At this time, a distribution of image feature quantities is calculated only when a correlation (such as a correlation ratio) which is already calculated separately in a combination of an image interpretation item (or a disease name) and an image feature quantity is larger than or equal to a predetermined threshold value. This is because, when a distribution of image feature quantities in cases whose image interpretation reports do not include the given image interpretation item (or the disease name) is also deviated as in the graph (a) of FIG. 22 showing the distribution of the image feature quantities in the cases whose image interpretation reports include the given image interpretation item (or the disease name), the given image interpretation item (or the given disease name) does not characterize the distribution shape of the image feature quantities.

As a specific representation approach of such a distribution, it is possible to use, for example, a Gaussian Mixture Model. In addition, as for the calculation of the distribution, it is possible to use an Expectation Maximization (EM) algorithm. The obtained distribution parameter is stored in an image interpretation knowledge database 110 in the form as shown in FIG. 23. The cell that is the cross point of an image interpretation item 1 and an image feature quantity 1 stores dim-dimensional parameters. In the case of a one-dimensional Gaussian Mixture Model, the parameters are the number of normal distributions, the average and the standard deviation of each of the normal distributions, and the weight to each of the normal distributions. In FIG. 23, the other cells are blanks. However, in reality, distribution parameters are stored in (the) remaining cells in the same manner as long as the separately-calculated correlations are larger than or equal to the predetermined threshold value. In addition, the complexities of distributions vary depending on the combinations of an image interpretation items and an image feature quantity, the numbers of the parameters in the distributions may vary. Alternatively, it is also possible to represent such distributions using another approach such as the Parzen Estimation.

(2) Distribution of Image Feature Quantities Corresponding to Disease Name

In FIG. 24, the graph (a) shows the distribution of the values indicating the image feature quantity "Average luminance in tumor inside area in arterial phase" observed in images of liver tumors respectively associated in cases with image interpretation reports each of which includes the disease name "Hepatocellular carcinoma". In FIG. 24, the graph (b) shows the distribution of the values indicating the image feature quantity "Average luminance in tumor inside area in arterial phase" observed in images of liver tumors respectively associated in cases with image interpretation reports each of which includes the disease name "Cyst". When the disease name is "Hepatocellular carcinoma", an artery lesion with high contrast is observed in a contrast arterial phase (a CT value increases), and thus a distribution such as the distribution in the graph (a) of FIG. 24 is obtained. When the disease name is "Cyst", no such an artery lesion with high contrast is observed even in a contrast arterial phase, and thus a distribution such as the distribution in the graph (b) of FIG. 24 is obtained. As for the calculation of such a distribution, it is possible to use the same approach as in the cases whose image interpretation reports respectively include the image interpretation item. At this time, as described earlier regarding the image interpretation item, a distribution of image feature quantities is calculated only when a correlation which is already calculated separately in a combination of a disease name and an image feature quantity is larger than or equal to a predetermined threshold value. The obtained distribution parameter is stored in an image interpretation knowledge database 110 in the form as shown in FIG. 25.

By performing the process in Step S14 according to the above approach, the following are respectively obtained: the correlations between image feature quantities and image interpretation items as in FIG. 13; the correlations between image feature quantities and disease names as in FIG. 14; the correlations between image interpretation items and disease names as in FIG. 15; the distribution parameters of the image feature quantities regarding the image interpretation items in FIG. 23; and the distribution parameters of the image feature quantities regarding the disease names in FIG. 25. In addition, the obtained correlations and distribution parameters are stored in the image interpretation knowledge database 110.

(Similar Case Search)

Hereinafter, a procedure for a similar case search is described with reference to the flowchart of FIG. 16.

The operations performed in Step S20 to Step S24 are the same as those in Embodiment 1.

In Step S25, the weight determining unit 170 and the similar case search unit 180 search the case database for a similar case, based on the interpretation target image and the image interpretation report written by the doctor.

In addition to the similar case search with weights using the image interpretation item and disease name extracted in the search (Step S24) described in Embodiment 1, Embodiment 2 verifies the validities of the image interpretation items and the disease names extracted in Step S24, based on the image interpretation knowledge (the distributions of the image feature quantities regarding the image interpretation item or the disease name) extracted in advance (Step S14) by the weight determining unit 170.

Here, in Step S14, the image interpretation knowledge database 110 stores in advance the correlations between two of three data types that are the image feature quantity, the image interpretation item, and the disease name in FIG. 13, FIG. 14, and FIG. 15, the distribution of the image feature quantities regarding the image interpretation items in FIG. 23, and the distribution of the image feature quantities regarding the disease names in FIG. 25. In addition, in S21, the image interpretation report in FIG. 26 is written in advance by a doctor. In Step S23, the image feature quantities are extracted from each of the interpretation target images. In Step S24, the image interpretation items and the disease names in FIG. 27 are extracted in advance.

Figure 27:
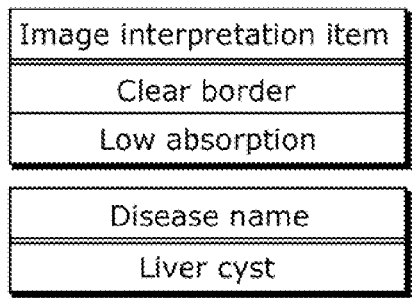
FIG. 27 is a diagram showing image interpretation items and a disease name extracted from the image interpretation report according to Embodiment 2.

Among the image interpretation items in FIG. 27, the "Clear border" is considered. The weight determining unit 170 obtains the distribution of all the image feature quantities corresponding to the image interpretation item "Clear border", from the data in FIG. 23 stored in the image interpretation knowledge database 110. At this time, it is impossible to obtain the image feature quantities having a small correlation with the image interpretation item "Clear border" because no distribution parameters thereof are stored. As for the image feature quantities of the same kind, a verification is made as to the correlation between the obtained feature quantity distribution and the image feature quantities extracted in Step S23. When the value of each of the image feature quantities extracted in Step S23 is $x_1$ the validity $(x_1)$ of the image feature quantity $x_1$ is calculated by integrating a probability density function p (i) within a range of a minute width $\pm\delta$ centering $x_1$ as in Expression 10. The validity $(x_1)$ is a kind of a likelihood. Based on the validity $(x_1)$ value, the validity of the image interpretation item "Clear border" written by the doctor is determined.

[Math. 10]

$$\text{validity}(x_1) = \sum_{i=x_1-\delta}^{x_1+\delta} p(i) \quad \text{(Expression 10)}$$

Figure 28:
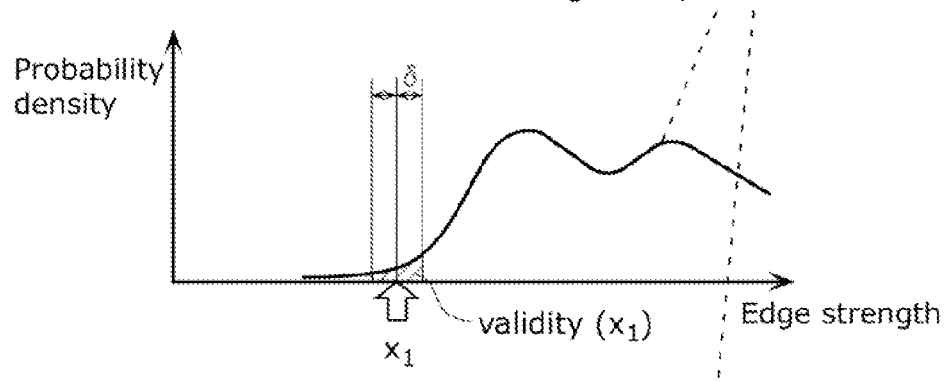
FIG. 28 is an illustration of how to determine validities of an image interpretation item input by users (such as doctors), based on constituent graphs (a) and (b) respectively showing image feature quantity distributions regarding the image interpretation item according to Embodiment 2.

FIG. 28 is an illustration of how to determine the validities of image interpretation items as described above. The validity of the image interpretation item "Clear border" in the case of the graph (b) of FIG. 28 where the image feature quantity $x_2$ is extracted is higher than the validity of the image interpretation item "Clear border" in the case of the graph (a) of FIG. 28 where the image feature quantity $x_1$ is extracted.

Since plural types of image feature quantities are present, the validity of the image interpretation item "Clear border" can be evaluated based on the plural types of image feature quantities. Here, the validity of the image interpretation item is determined based on several top correlations between the respective image feature quantities and the image interpretation item calculated in Step S14. When all the validities of these several top image features are larger than or equal to the threshold value, the image interpretation item "Clear border" is finally determined to be "Valid". The number corresponding to the several top and the threshold value are calculated in advance. Although the condition (AND condition) that "all the validities of these several top image features are larger than or equal to the threshold value" is used above, it is also good to determine that the "Clear border" as the image interpretation item is finally determined to be "Valid" under the condition (OR condition) that "any of the validities: of these several top image features is larger than or equal to the threshold value".

The weight determining unit 170 determines the validity of the remaining image interpretation item "Low absorption" in FIG. 27 and the validity of the disease name "Liver cyst".

In addition, although the validities of the disease names are determined based on the correlations (image feature quantity distributions) between the image feature quantities and the disease names as shown in FIG. 24, it is also good to determine the validities based on the correlations between the image interpretation items and the disease names as shown in FIG. 15.

Next, weighted distance calculations are made in a similar case search, and a similar case is searched out. These calculations are the same as in Embodiment 1, and thus the same descriptions are not repeated here.

The following describes how to utilize the results of the determinations on the validities of the image interpretation items and the disease names calculated by the weight determining unit 170.

Figure 29:
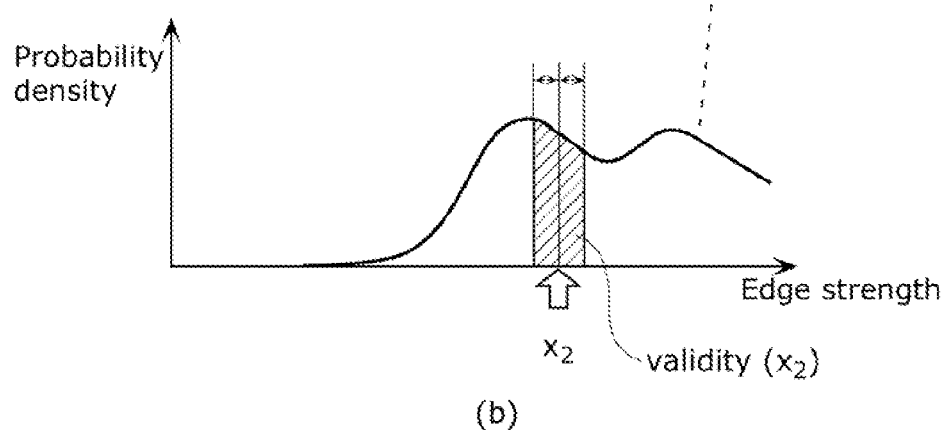
FIG. 29 is a diagram showing an example of an input image interpretation report with modifications according to Embodiment 2.

The report input and output unit 140 modifies the image interpretation report already input using the input means of the report input and output unit 140 in the image interpretation, and displays the modified image interpretation report on the display means of the report input and output unit 140. For example, as shown in FIG. 29, the report input and output unit 140 displays image interpretation items and a disease name such that the disease name and one of the image interpretation items whose validities are determined to be low (smaller than or equal to the threshold value) are differentiated from the other image interpretation item whose validity is determined to be high (larger than or equal to the threshold value). In FIG. 29, the three words each enclosed by a rectangle are the extracted disease name and the extracted image interpretation items. Among these three words, the highlighted "Clear border" and "Liver cyst" are one of the extracted image interpretation items and the disease name whose validities are determined to be low. Such differentiation in display allows the doctor to simultaneously recognize which description input by himself or herself in the image interpretation report is used as the basis for the similar case search and recognize which descriptions are determined to have a low validity by the similar case searching apparatus. Furthermore, the doctor can interpret the interpretation target images again with reference to the definitive diagnosis of the searched-out similar case. Although the image interpretation items and the disease name are not differentiated based on their data types in the display described above, it is also good to display these two types of information in a distinguishable manner. In addition, although the validities are shown in a binary representation (highlighted or not), it is also good to show the validities in a multi-value representation based on the magnitudes of the validity values.

In the starting portion of this embodiment, the following description is made: "In the case of a fresh doctor who does not have much experience, the descriptions (especially focus points) written in an image interpretation report may be inappropriate. In this case, an image search reflecting the inappropriate focus points is inevitably performed.", and "However, even in this case, there is no possibility that a totally different case is searched out because a similar image search is executed (from another viewpoint) based on image feature quantities obtained from the target image although these image feature quantities are not the image feature quantities that should be focused on." Furthermore, it is possible to prevent an image search reflecting inappropriate focus points by adding weights of 0 to the image feature quantities corresponding to the image interpretation item and the disease name determined to have low validities and performing the image search based on the weighted image feature quantities. For example, in FIG. 19, $w_{a,i}=0$ is set when the image interpretation item "Early stain" is determined to have a low validity based on the image features extracted from the interpretation target image. Likewise, it is also good to determine that descriptions contradictory to the image interpretation knowledge in FIG. 13, FIG. 14, FIG. 15, FIG. 23, and FIG. 25 stored in the image interpretation knowledge database 110 to have low validities, and add weights of 0 thereto. When a many number of image interpretation items and disease names are extracted, searches are executed using weights to the image feature quantities corresponding to the remaining image interpretation items and disease names determined to have high validities. When a few number of disease names are extracted (when the number is smaller than a predetermined threshold value), case searches are executed by adding standard weights to the image feature quantities.

Figure 30:
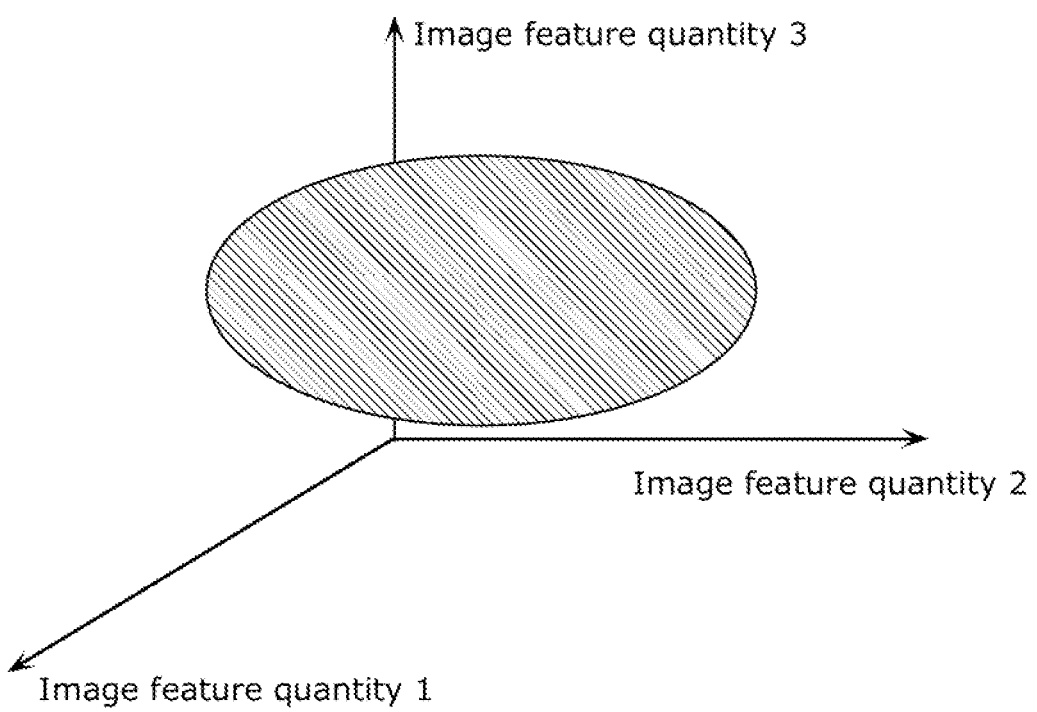
FIG. 30 is an illustration of a distribution of image feature quantities regarding an image interpretation item according to Embodiment 2.

The above descriptions are given of an example where the image interpretation knowledge includes the distribution of the values of image feature quantities of "one kind" corresponding to the given image interpretation item or disease name. However, it is also good that the image interpretation knowledge include a distribution of the values of image feature quantities of "two or more kinds". FIG. 30 shows an example of a distribution of the values of image feature quantities of three kinds corresponding to a given image interpretation item or disease name. As for modeling of the distribution, it is possible to use a Gaussian Mixture Model, the Parzen Estimation, or the like, as in the earlier descriptions. In addition, when the distribution of image feature quantities in the case of a given image interpretation item is included and the distribution of image feature quantities in the case of the given image interpretation item is not included are separated appropriately on a feature quantity space, it is also possible to learn an identification algorithm for separating these two distributions using a pattern identifying approach such as Support Vector Machine (SVM), and to determine the validities of the image feature quantities based on the results of the identification by the identification algorithm.

As in Embodiment 1, Embodiment 2 makes it possible to perform a similar case search involving weighted distance calculations based on at least one of the image interpretation items and disease name extracted from the image interpretation reports, and thus the similar case search can reflect doctor focus points. Furthermore, in Embodiment 2, among the image interpretation items and the disease names that are written in the target image interpretation reports and used for the similar case search, it is possible to present, to the doctor, the bases for the similar case search and one or more image interpretation report portions (one or more of the image interpretation items and/or one or more of the disease names) each having a low validity by displaying the one or more portions each having the low validity and one or more portions each having a high validity in a distinguishable manner.

Embodiments 1 and 2 describe examples in which searches are made for cases each composed of medical images and an image interpretation report of the medical images. However, search targets in the present disclosure are not limited to the cases. It is also possible to determine, as search targets, data sets each of which is composed of an image and text data of the image. For example, it is also possible to determine, as search targets, data sets each of which is composed of a plant image and explanations of the plant image. In this case, it is possible to calculate weights to the image feature quantities focused by the user when preparing the explanations, by using image feature quantities of the plant image (for example, the number of petals, the width of a stem, and the like) instead of image feature quantities of a medical image, and using the explanations of the plant image instead of an image interpretation report of the medical image, and search plant images based on the weighted image feature quantities.

Figure 31:
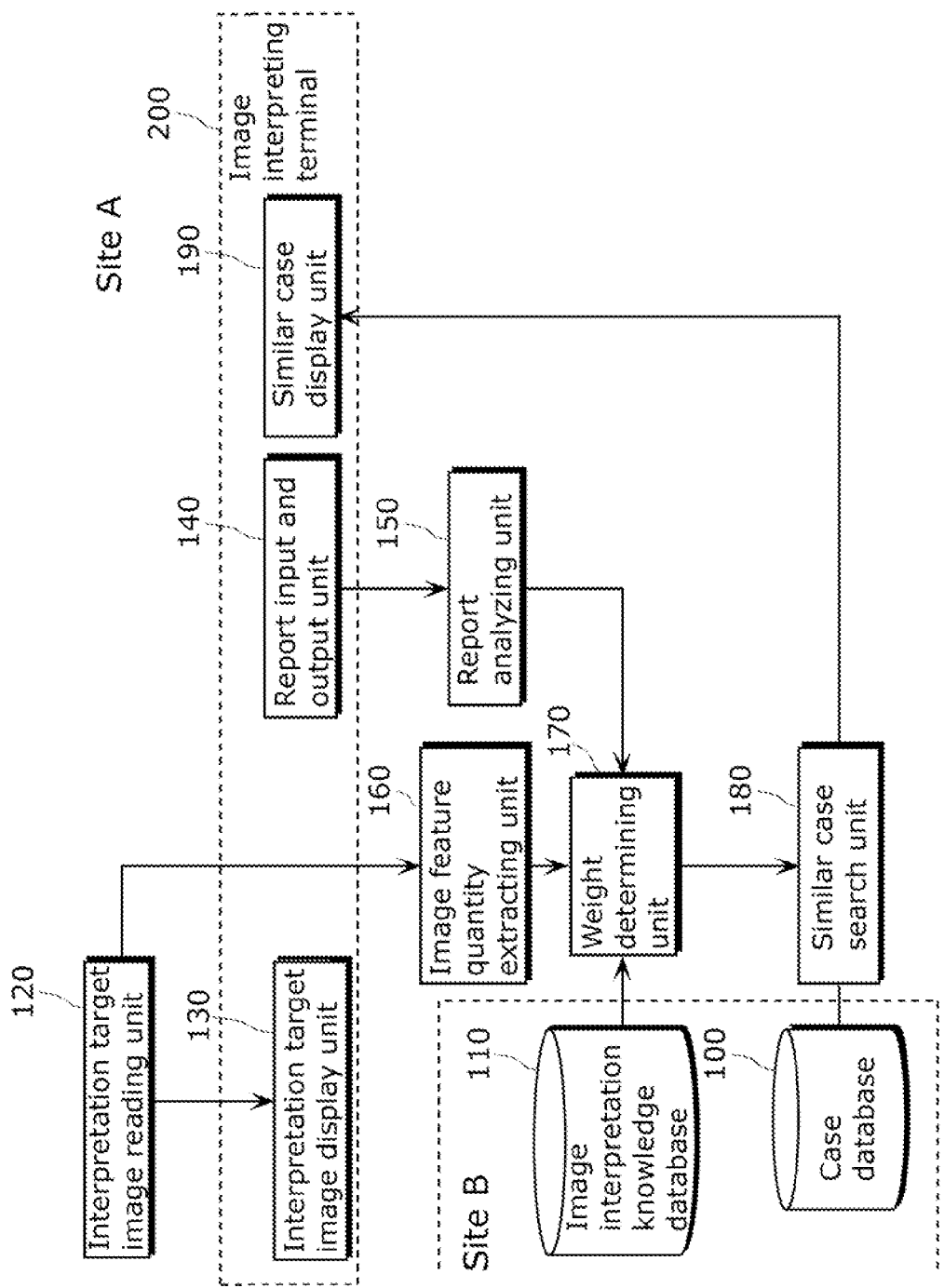
FIG. 31 is a block diagram of another structure of a similar case searching apparatus according to a variation of the present disclosure.

As shown in FIG. 31, it is not always necessary that the image interpretation knowledge database 110 and the case database 100 are included in the similar case search apparatus. In other words, these databases may be provided at a site B different from a site A in which the similar case searching apparatus is present. In this case, the weight determining unit 170 and the similar case search unit 180 of the similar case searching apparatus are respectively connected to the image interpretation knowledge database 110 and the case database 100 via a network.

Figure 32:
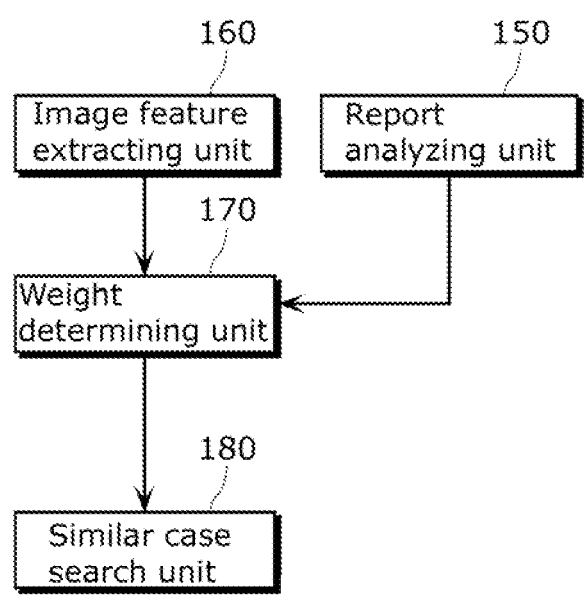
FIG. 32 is a block diagram of essential structural elements of a similar case searching apparatus according to the present disclosure.

In addition, as shown in FIG. 32, the essential structural elements of the similar case searching apparatus are the report analyzing unit 150, the image feature quantity extracting unit 160, the weight determining unit 170, and the similar case search unit 180, and thus the other structural elements are not always necessary.

In addition, each of the above apparatuses may be configured as, specifically, a computer system including a microprocessor, a ROM, a RAM, a hard disk unit, a display unit, a keyboard, a mouse, and so on. A computer program is stored in the RAM or hard disk unit. The respective apparatuses achieve their functions through the microprocessor's operations according to the computer program. Here, the computer program is configured by combining plural instruction codes indicating instructions for the computer, so as to allow execution of predetermined functions.

In other words, this program is for causing a computer to executes the steps of the similar case searching method. This similar case searching method is for searching a case database for a similar case data item similar to a target case data item of a target case to be diagnosed, the case database storing a plurality of case data items, each of the case data items and the target case data item including one or more medical images and an image interpretation report that is a document data item indicating interpretations of the medical images, and the similar case searching method comprises: extracting a plurality of image feature quantities from one of the medical images which is an interpretation target image; extracting one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image; determining a weight to each of the image feature quantities extracted in the extracting, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and searching the case database for the similar case data item including a similar image similar to the interpretation target image, by weighting each of the image feature quantities in a first set extracted from the interpretation target image in the extracting and a corresponding one of the image feature quantities in a second set extracted from the medical images included in the case data items registered in the case database, using the weight to the image feature quantity determined in the determining, and comparing the weighted image feature quantities in the first set and the weighted image feature quantities in the second set.

Furthermore, a part or all of the structural elements of the respective apparatuses may be configured with a single system-LSI (Large-Scale Integration). The system-LSI is a super-multi-function LSI manufactured by integrating constituent units on a single chip, and is specifically a computer system configured to include a microprocessor, a ROM, a RAM, and so on. A computer program is stored in the RAM. The system-LSI achieves its/their function(s) through the microprocessor's operations according to the computer program.

Furthermore, a part or all of the structural elements constituting the respective apparatuses may be configured as an IC card which can be attached to and detached from the respective apparatuses or as a stand-alone module. The IC card or the module is a computer system configured from a microprocessor, a ROM, a RAM, and so on. The IC card or the module may also be included in the aforementioned super-multi-function LSI. The IC card or the module achieves its/their function(s) through the microprocessor's operations according to the computer program. The IC card or the module may also be implemented to be tamper-resistant.

In addition, the respective apparatuses and their equivalents according to the present disclosure may be realized as methods including the steps corresponding to the unique units of the apparatuses. Furthermore, these methods according to the present disclosure may also be realized as computer programs for executing these methods or digital signals of the computer programs.

Such computer programs or digital signals according to the present disclosure may be recorded on computer-readable non-volatile recording media such as flexible discs, hard disks, CD-ROMs, MOs, DVDs, DVD-ROMs, DVD-RAMs, BDs (Blu-ray Disc (registered trademark)), and semiconductor memories. In addition, these methods according to the present disclosure may also be realized as the digital signals recorded on these non-volatile recording media.

Furthermore, these methods according to the present disclosure may also be realized as the aforementioned computer programs or digital signals transmitted via a telecommunication line, a wireless or wired communication line, a network represented by the Internet, a data broadcast, and so on.

The apparatuses (or computers or a computer system) according to the present disclosure may also be implemented as a computer system including a microprocessor and a memory, in which the memory stores the aforementioned computer program and the microprocessor operates according to the computer program.

Furthermore, it is also possible to execute another independent computer system by transmitting the programs or the digital signals recorded on the aforementioned non-transitory recording media, or by transmitting the programs or digital signals via the aforementioned network and the like.

Similar case searching apparatus according to one or more aspects of the present disclosure have been described based on the exemplary embodiments. However, these exemplary embodiments do not limit the inventive concept, the scope of which is defined in the appended Claims and their equivalents. Those skilled in the art will readily appreciate that various modifications may be made in these exemplary embodiments and other embodiments may be made by arbitrarily combining some of the structural elements of different exemplary embodiments without materially departing from the principles and spirit of the inventive concept, the scope of which is defined in the appended Claims and their equivalents.

INDUSTRIAL APPLICABILITY

One or more exemplary embodiments of the present disclosure are applicable to similar case searching apparatuses which search and present similar cases provided to users (such as doctors) for reference, image interpretation training apparatuses for fresh doctors, and the like.

The invention claimed is:

1. A similar case searching apparatus which searches a case database for a similar case data item similar to a target case data item of a target case to be diagnosed, the case database storing a plurality of case data items, and each of the case data items and the target case data item including one or more medical images and an image interpretation report that is a document data item indicating interpretations of the medical images, said similar case searching apparatus comprising:

an image feature quantity extracting unit configured to extract a plurality of image feature quantities from one of the medical images which is an interpretation target image;

a report analyzing unit configured to extract one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image;

a weight determining unit configured to determine a weight to each of the image feature quantities extracted by said image feature quantity extracting unit, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and a similar case searching unit configured to search the case database for the similar case data item including a similar image similar to the interpretation target image, by weighting each of the image feature quantities in a first set extracted from the interpretation target image by said image feature quantity extracting unit and a corresponding one of the image feature quantities in a second set extracted from the medical images included in the case data items registered in the case database, using the weight to the image feature quantity determined by said weight determining unit, and comparing the weighted image feature quantities in the first set and the weighted image feature quantities in the second set, wherein when said report analyzing unit extracts, for a current one of the image feature quantities extracted by said image feature quantity extracting unit, both of the at least one image interpretation item and the disease name from the target image interpretation report, said weight determining unit is configured to determine, as the weight to the current image feature quantity, a product of a value indicating a correlation between the current image feature quantity and the at least one image interpretation item extracted by said report analyzing unit and a value indicating a correlation between the at least one image interpretation item and the disease name extracted by said report analyzing unit, based on the two-data correlation information for the current image feature quantity.

2. The similar case searching apparatus according to claim 1, wherein the two-data correlation information further indicates a correlation between the at least one image interpretation item and the disease name extracted from the image interpretation report.

3. The similar case searching apparatus according to claim 1, when said report analyzing unit extracts, for a current one of the image feature quantities extracted by said image feature quantity extracting unit, the at least one image interpretation item from the target image interpretation report, said weight determining unit is configured to determine, as the weight to the current image feature quantity, a value indicating a correlation between the current image feature quantity and the at least one image interpretation item extracted by said report analyzing unit, based on the two-data correlation information for the current image feature quantity.

4. The similar case searching apparatus according to claim 1, when said report analyzing unit extracts, for a current one of the image feature quantities extracted by said image feature quantity extracting unit, the disease name from the target image interpretation report, said weight determining unit is configured to determine, as the weight to the current image feature quantity, a value indicating a correlation between the at least one image interpretation item and the disease name extracted by said report analyzing unit, based on the two-data correlation information for the current image feature quantity.

5. A similar case searching apparatus which searches a case database for a similar case data item similar to a target case data item of a target case to be diagnosed, the case database storing a plurality of case data items, and each of the case data items and the target case data item including one or more medical images and an image interpretation report that is a document data item indicating interpretations of the medical images, said similar case searching apparatus comprising:

an image feature quantity extracting unit configured to extract a plurality of image feature quantities from one of the medical images which is an interpretation target image;

a report analyzing unit configured to extract one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image;

a weight determining unit configured to determine a weight to each of the image feature quantities extracted by said image feature quantity extracting unit, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and a similar case searching unit configured to search the case database for the similar case data item including a similar image similar to the interpretation target image, by weighting each of the image feature quantities in a first set extracted from the interpretation target image by said image feature quantity extracting unit and a corresponding one of the image feature quantities in a second set extracted from the medical images included in the case data items registered in the case database, using the weight to the image feature quantity determined by said weight determining unit, and comparing the weighted image feature quantities in the first set and the weighted image feature quantities in the second set;

wherein said weight determining unit is further configured to determine that each of the at least one image interpretation item or the disease name extracted by said report analyzing unit has a higher validity as a current one of the image feature quantities corresponding to the at least one image interpretation item or the disease name and extracted by said image feature quantity extracting unit has a higher likelihood, based on a probability distribution data prepared for a corresponding image feature quantity included in a medical image based on which an image interpretation report including at least one corresponding image interpretation item or the disease name is made.

6. The similar case searching apparatus according to claim 5, further comprising a display unit configured to display the target image interpretation report, wherein said display unit is configured to display the at least one image interpretation item or the disease name included in the target image interpretation report in a visually distinguishable manner, based on a degree of validity of the at least one image interpretation item or the disease name determined by said weight determining unit.

7. A similar case searching method of searching a case database for a similar case data item similar to a target case data item of a target case to be diagnosed, the case database storing a plurality of case data items, and each of the case data items and the target case data item including one or more medical images and an image interpretation report that is a document data item indicating interpretations of the medical images, said similar case searching method comprising:

extracting a plurality of image feature quantities from one of the medical images which is an interpretation target image;

extracting one of at least one image interpretation item and a disease name from the image interpretation report which is a target image interpretation report made by a user in the interpretation of the interpretation target image, the image interpretation item being a character string indicating a feature of a medical image and the disease name being obtained as a result of a diagnosis made by a user based on the medical image;

determining a weight to each of the image feature quantities extracted in said extracting, based on two-data correlation information that is prepared information defining a correlation between each of the image feature quantities extracted from the medical image and one of the at least one image interpretation item and the disease name extracted from the image interpretation report of the medical image, such that the weight to the extracted image feature quantity is larger as the correlation between the image feature quantity and the one of the at least one image interpretation item and the disease name is higher; and searching the case database for the similar case data item including a similar image similar to the interpretation target image, by weighting each of the image feature quantities in a first set extracted from the interpretation target image in said extracting and a corresponding one of the image feature quantities in a second set extracted from the medical images included in the case data items registered in the case database, using the weight to the image feature quantity determined in said determining, and comparing the weighted image feature quantities in the first set and the weighted image feature quantities in the second set;

wherein said weight determining further involves determining that each of the at least one image interpretation item or the disease name extracted by said report analyzing has a higher validity as a current one of the image feature quantities corresponding to the at least one image interpretation item or the disease name and extracted by said image feature quantity extracting has a higher likelihood, based on a probability distribution data prepared for a corresponding image feature quantity included in a medical image based on which an image interpretation report including at least one corresponding image interpretation item or the disease name is made.

8. A non-transitory computer-readable recording medium for use in a computer, said recording medium having a computer program recorded thereon for causing the computer to execute the similar case searching method according to claim 7.

* * * * *